United States Patent
Akiyoshi et al.

(10) Patent No.: US 9,234,186 B2
(45) Date of Patent: Jan. 12, 2016

(54) STAR-WORM LUCIFERASE

(71) Applicants: OLYMPUS CORPORATION, Tokyo (JP); Nimura Genetic Solutions Co., Ltd., Tokyo (JP); Perak State Development Corporation, Ipoh, Perak Darul Ridzuan (MY)

(72) Inventors: Ryutaro Akiyoshi, Hachioji (JP); Katsunori Ogo, Hachioji (JP); Hirobumi Suzuki, Hachioji (JP)

(73) Assignees: OLYMPUS CORPORATION, Tokyo (JP); NIMURA GENETIC SOLUTIONS CO., LTD., Tokyo (JP); PERAK STATE DEVELOPMENT CORPORATION, Ipoh, Perak Darul Ridzuan (MY)

( * ) Notice: Subject to any disclaimer, the term of this patent is extended or adjusted under 35 U.S.C. 154(b) by 0 days.

(21) Appl. No.: 14/025,950

(22) Filed: Sep. 13, 2013

(65) Prior Publication Data
US 2014/0073031 A1 Mar. 13, 2014

Related U.S. Application Data

(63) Continuation of application No. PCT/JP2012/056802, filed on Mar. 12, 2012.

(30) Foreign Application Priority Data

Mar. 15, 2011 (MY) .............................. PI2011001154

(51) Int. Cl.
*C12N 9/02* (2006.01)

(52) U.S. Cl.
CPC .................................. *C12N 9/0069* (2013.01)

(58) Field of Classification Search
None
See application file for complete search history.

(56) References Cited

U.S. PATENT DOCUMENTS

| | | |
|---|---|---|
| 2006/0035286 A1 | 2/2006 | Ohmiya et al. |
| 2007/0105172 A1* | 5/2007 | Ohmiya et al. .................. 435/8 |

FOREIGN PATENT DOCUMENTS

| | | |
|---|---|---|
| CN | 1784496 A | 6/2006 |
| EP | 1 621 634 A1 | 2/2006 |
| JP | 2006-301599 A | 11/2006 |
| WO | WO 03/042693 A2 | 5/2003 |
| WO | WO 2004099421 A1 * | 11/2004 |
| WO | WO 2006/088109 A1 | 8/2006 |

OTHER PUBLICATIONS

Viviani et al., "Cloning, sequence analysis, and expression of active Phrixothrix railroad-worms luciferases: Relationship between bioluminescence spectra and primary structures", Biochemistry, vol. 38, No. 26, pp. 8271-8279, 1999.*

International Search Report dated Jul. 16, 2012 issued in PCT/JP2012/056802.

Chinese Office Action dated Jul. 2, 2015 received from Application No. 201280012817.X, together with an English-language translation.

* cited by examiner

*Primary Examiner* — Robert Mondesi
*Assistant Examiner* — Richard Ekstrom
(74) *Attorney, Agent, or Firm* — Scully, Scott, Murphy & Presser, P.C.

(57) ABSTRACT

The present invention relates to a luciferase derived from a star-worm belonging to genus *Diplocladon*, the luciferase inducing luminescence such that a maximum luminous wavelength falls within a range of 557 to 562 nm over the entire pH range of 5.5 to 8.0, or the luciferase inducing luminescence having 1.5 times the luminous intensity of luminescence induced by *Photinus pyralis* firefly luciferase.

3 Claims, 3 Drawing Sheets

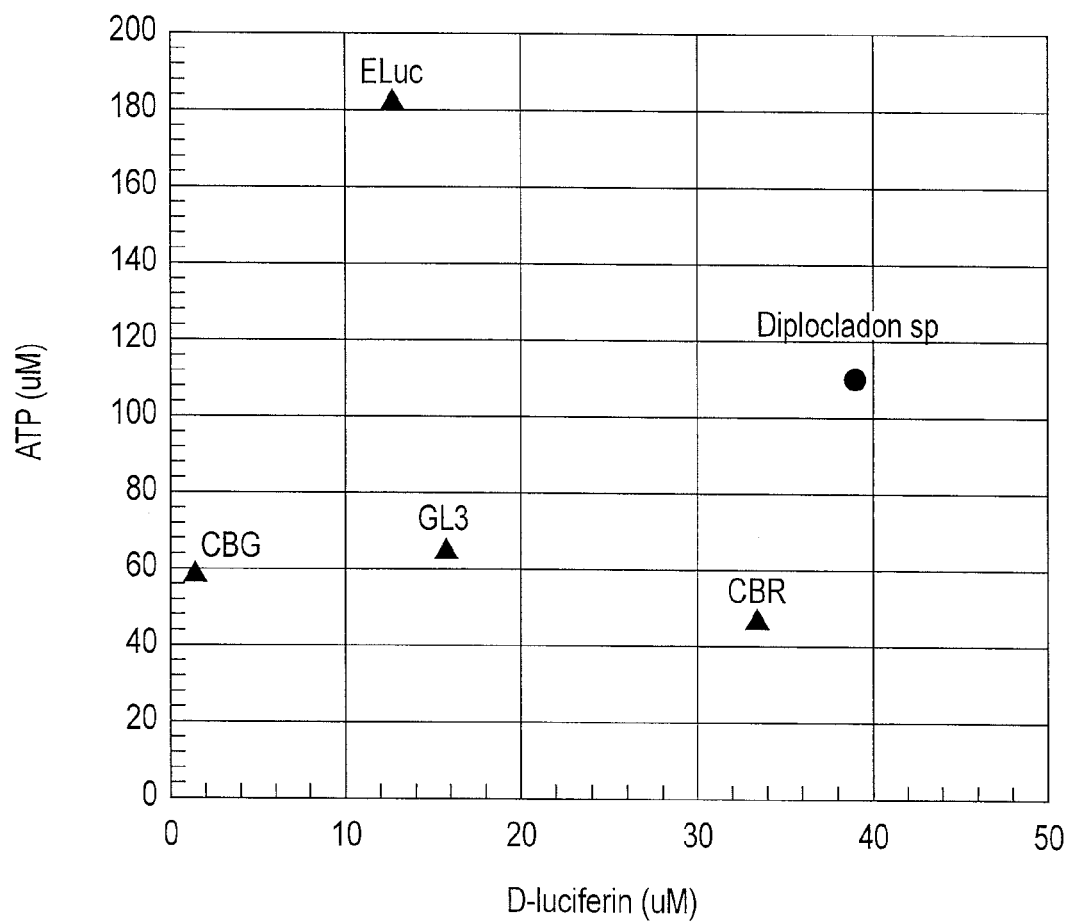
F I G. 2

SEQUENCE LISTING

```
<160> NUMBER OF SEQ ID NOS: 15

<210> SEQ ID NO 1
<211> LENGTH: 543
<212> TYPE: PRT
<213> ORGANISM: Diplocladon sp.

<400> SEQUENCE: 1

Met Pro Asn Glu Ile Val Leu His Gly Ala Lys Pro Arg Asp Pro Leu
1               5                   10                  15

Asp Leu Gly Thr Ala Gly Ser Gln Leu Phe Arg Ser Leu Thr Gln Phe
            20                  25                  30

Ser Tyr Leu Arg Glu Ala Leu Val Asp Ala His Thr Glu Gln Val Val
        35                  40                  45

Ser Tyr Ala Asp Ile Leu Glu Asn Ser Cys Arg Leu Ala Ile Cys Phe
    50                  55                  60

Glu Lys Tyr Gly Leu Arg Gln Asn Ser Val Ile Ala Val Cys Ser Glu
65                  70                  75                  80

Asn Ser Ala Ile Phe Phe Tyr Pro Val Ile Ala Ala Leu Tyr Met Gly
                85                  90                  95

Ile Ile Thr Ala Thr Val Asn Asp Asn Tyr Thr Glu Arg Glu Leu Phe
            100                 105                 110

Asp Thr Leu Asn Ile Ser Lys Pro Glu Leu Val Phe Cys Ser Lys Lys
        115                 120                 125

Ala Ile Lys Asn Leu Thr Gln Leu Lys Asn His Ile Asp Phe Ile Lys
    130                 135                 140

Lys Leu Val Val Leu Asp Ser Asp Glu Asp Ile Gly Glu Val Glu Ser
145                 150                 155                 160

Leu Ala Asn Phe Met Lys Arg Tyr Ser Glu Ser Val Ile Asp Val Arg
                165                 170                 175

Asn Phe Lys Pro Arg Asp Phe Asp Ala Lys Glu Gln Val Ala Leu Ile
```

```
                    180              185                190
Met Ser Ser Ser Gly Thr Thr Gly Leu Pro Lys Gly Val Val Leu Thr
                195              200              205

His Arg Asn Leu Ser Val Arg Phe Val His Cys Lys Asp Pro Leu Phe
                210              215              220

Gly Thr Arg Thr Val Pro Ser Thr Ser Ile Leu Ser Ile Val Pro Phe
225              230              235              240

His His Ala Phe Gly Met Phe Thr Thr Leu Ser Tyr Phe Ile Val Gly
                245              250              255

Leu Arg Val Ile Leu Leu Lys Arg Phe Glu Glu Glu Phe Phe Leu Ser
                260              265              270

Thr Ile Glu Lys Tyr Arg Ile Pro Thr Ile Val Leu Ala Pro Pro Val
                275              280              285

Met Val Phe Leu Ala Lys Ser Pro Leu Val Asp Gln Tyr Asp Val Ser
                290              295              300

Ser Ile Arg Glu Val Ala Thr Gly Gly Ala Pro Val Gly Ile Glu Val
305              310              315              320

Ala Glu Ala Val Ala Lys Arg Leu Lys Ile Asn Gly Ile Leu Gln Gly
                325              330              335

Tyr Gly Leu Thr Glu Thr Cys Cys Ala Val Leu Ile Thr Pro His Asp
                340              345              350

His Val Lys Thr Gly Ser Thr Gly Lys Val Ala Pro Tyr Val Gln Ala
                355              360              365

Lys Val Val Asp Leu Ser Thr Gly Lys Ser Leu Gly Pro Asn Lys Arg
                370              375              380

Gly Glu Leu Cys Phe Lys Ser Glu Ile Ile Met Lys Gly Tyr Phe Asn
385              390              395              400

Asn Ile Lys Ala Thr Glu Glu Ala Ile Asp Lys Glu Gly Trp Leu His
                405              410              415

Ser Gly Asp Val Gly Tyr Tyr Asp Glu Asp Gly His Phe Tyr Val Val
                420              425              430

Asp Arg Leu Lys Glu Leu Ile Lys Tyr Lys Gly Tyr Gln Val Ala Pro
                435              440              445

Ala Glu Leu Glu Trp Leu Leu Leu Gln His Pro Ala Ile Lys Asp Ala
                450              455              460

Gly Val Thr Gly Val Pro Asp Glu Ala Ala Gly Glu Leu Pro Gly Ala
465              470              475              480

Cys Ile Val Leu Glu Glu Gly His Ser Leu Thr Glu Gln Gly Val Ile
                485              490              495

Glu Tyr Val Ala Glu Arg Val Ser Pro Thr Lys Arg Ile Arg Gly Gly
                500              505              510

Val Val Phe Val Asp Asp Ile Pro Lys Gly Ala Thr Gly Lys Leu Val
                515              520              525

Arg Ser Glu Leu Arg Arg Met Leu Ser Gln Lys Lys Ser Lys Leu
                530              535              540

<210> SEQ ID NO 2
<211> LENGTH: 1632
<212> TYPE: DNA
<213> ORGANISM: Diplocladon sp.

<400> SEQUENCE: 2
atgccgaatg aaatcgtttt acatggagcc aaaccgcgag atccattaga cctgggaact    60
gcaggaagtc aattatttag gtctttgacg caatttcctt atttaagaga agctctggtc   120
```

-continued

```
gacgctcata ctgagcaagt ggtatcttac gcggatatct tagaaaacag ttgccgtcta    180
gctatatgct ttgagaaata tggattacgc caaaatagtg tcatagcagt atgcagcgaa    240
aatagcgcga tcttttttcta ccccgtaatc gccgctttat atatgggtat cataacagca   300
acagtaaatg ataactacac cgaaagggaa ttattcgaca ctttaaatat ttcgaaacct    360
gaactggtat tctgttcgaa gaaggcgatt aaaaacttga cgcaattgaa gaatcacatc    420
gattttatta aaaagctcgt agttttggat agtgatgaag acataggtga agtcgaatct    480
cttgccaact ttatgaaacg ctattcagaa tctgttattg atgtgagaaa ctttaagcct    540
cgcgattttg atgctaaaga acaagttgcc ttaatcatgt cgtcatcagg aacaactgga    600
ttacctaaag gagtcgttct aacccataga aatttgagcg ttcgctttgt acattgcaag    660
gacccgttat tcggcacaag gactgtccct tcaacttcaa ttttatctat cgttcctttc    720
catcatgcgt ttggaatgtt tacgacgttg tcctatttta tagtaggact cagagtcata    780
ctactaaaaa gattcgaaga agaatttttc ttaagcacta ttgaaaagta cagaattcca    840
actatcgttc ttgcaccacc cgtaatggta ttcctagcca agagtccgtt agtcgatcag    900
tacgatgtgt ccagtattag agaagttgct accggtggtg cacctgtcgg cattgaagtg    960
gcagaagctg ttgcgaaacg gctaaaaatt aatggaatac ttcaaggata cggtctaaca   1020
gagacatgtt gcgccgtatt aatcacccca cacgaccatg ttaaaacagg ttctactggg   1080
aaagtcgccc cgtacgtgca agcgaaagtt gtagatctta gcaccggaaa atctctaggg   1140
ccaaataaaa gaggagaact ttgctttaaa agcgagataa ttatgaaagg ttatttcaac   1200
aatataaagg ctacggaaga ggctatcgat aaagaaggat ggttacattc tggagatgtc   1260
gggtattatg atgaagatgg tcatttctac gtagtagatc gtttaaaaga acttatcaag   1320
tacaagggat atcaagttgc accggctgaa ttggaatggt tgcttttgca acatccagct   1380
atcaaagacg ccggtgttac tggcgttcct gacgaagctg ccggagaact tccgggtgct   1440
tgcatagtcc ttgaagaagg acatagtctt accgaacaag aagttattga atatgtagcc   1500
gaacgtgttt ctccaactaa acgtatacgt ggtggagtag ttttcgttga tgatataccc   1560
aaaggagcga ctggaaaact cgtcagaagt gaattacgga gaatgctttc tcagaagaaa   1620
tcgaaactat aa                                                        1632
```

<210> SEQ ID NO 3
<211> LENGTH: 1632
<212> TYPE: DNA
<213> ORGANISM: Diplocladon sp.

<400> SEQUENCE: 3

```
atgcccaacg agattgtgct gcacggcgcc aagcccaggg accctctgga tctgggcaca     60
gccggcagcc agctgttcag aagcctgacc cagttcagct acctgcgcga ggccctggtg    120
gacgcccaca ccgaacaggt ggtgtcctac gccgacatcc tggaaaacag ctgcagactg    180
gccatctgct tcgagaagta cggcctgcgg cagaacagcg tgatcgccgt gtgcagcgag    240
aacagcgcca tcttcttcta ccctgtgatc gccgccctgt acatgggcat catcaccgcc    300
accgtgaacg acaactacac cgagagagag ctgttcgaca ccctgaacat cagcaagccc    360
gagctggtgt tctgcagcaa gaaggccatc aagaatctga cccagctgaa gaaccacatc    420
gacttcatca gaaactggt ggtgctggac agcgacgagg acatcggcga ggtggaaagc    480
ctggccaact tcatgaagcg gtacagcgag tccgtgatcg acgtgcggaa cttcaagccc    540
```

```
cgggacttcg acgccaaaga acaggtggcc ctgatcatga gcagcagcgg caccaccggc      600
ctgcctaagg gcgtggtgct gacccaccgg aacctgagcg tgcgcttcgt gcactgcaag      660
gaccctctgt tcggcaccag aaccgtgccc agcaccagca tcctgagcat cgtgcccttc      720
caccacgcct tcggcatgtt caccaccctg agctacttca tcgtgggcct gagagtgatc      780
ctgctgaaga gattcgagga agagttcttc ctgagcacca tcgagaagta tcgcatcccc      840
accatcgtgc tggcccctcc cgtgatggtg ttcctggcca agagccccct ggtggatcag      900
tacgacgtgt ccagcatcag agaggtggcc accggcggag ccctgtgggg aattgaagtg      960
gccgaggccg tggccaagcg gctgaagatc aacggcatcc tgcagggcta cggcctgacc     1020
gagacatgct gcgccgtgct gatcaccccc cacgaccacg tgaaaaccgg cagcaccggc     1080
aaggtggccc cctatgtgca ggccaaggtg gtggacctgt ccaccggcaa gagcctgggc     1140
cccaacaagc ggggcgagct gtgcttcaag agcgagatca tcatgaaggg ctacttcaac     1200
aacatcaagg ccaccgagga agccatcgac aaagagggct ggctgcacag cggcgacgtg     1260
ggctactacg acgaggacgg ccacttctac gtggtggacc ggctgaaaga gctgatcaag     1320
tacaagggct accaggtggc acctgccgag ctggaatggc tgctgctgca gcaccccgcc     1380
atcaaggatg ccggcgtgac cggcgtgcca gatgaagctg ctggcgagct gcctggcgcc     1440
tgtatcgtgc tggaagaggg ccactccctg accgagcagg aagtgatcga gtacgtcgcc     1500
gagcgggtgt ccccccaccaa gagaatcaga ggcggcgtgg tgttcgtgga cgacatccct     1560
aagggcgcca caggcaagct ggtgcgcagc gagctgcggc ggatgctgag ccagaaaaag     1620
tccaagctgt ga                                                          1632
```

<210> SEQ ID NO 4
<211> LENGTH: 10
<212> TYPE: DNA
<213> ORGANISM: Artificial
<220> FEATURE:
<223> OTHER INFORMATION: kozak sequence

<400> SEQUENCE: 4 gccrccatgg                                                             10

<210> SEQ ID NO 5
<211> LENGTH: 37
<212> TYPE: DNA
<213> ORGANISM: Artificial
<220> FEATURE:
<223> OTHER INFORMATION: Home-Diplo(I)-BamHI-F primer

<400> SEQUENCE: 5
gccgggatcc gatgccgaat gaaatcgttt tacatgg                               37

<210> SEQ ID NO 6
<211> LENGTH: 38
<212> TYPE: DNA
<213> ORGANISM: Artificial
<220> FEATURE:
<223> OTHER INFORMATION: Home-Diplo(I)-stop-EcoRI-R primer

<400> SEQUENCE: 6
gccgggaatt cttatagttt cgatttcttc tgagaaag                              38

<210> SEQ ID NO 7
<211> LENGTH: 19
<212> TYPE: DNA
<213> ORGANISM: Artificial

```
<220> FEATURE:
<223> OTHER INFORMATION: M13-F(-29) primer

<400> SEQUENCE: 7
cacgacgttg taaaacgac                                              19

<210> SEQ ID NO 8
<211> LENGTH: 18
<212> TYPE: DNA
<213> ORGANISM: Artificial
<220> FEATURE:
<223> OTHER INFORMATION: M13 Reverse primer

<400> SEQUENCE: 8
ggataacaat ttcacagg                                               18

<210> SEQ ID NO 9
<211> LENGTH: 3257
<212> TYPE: DNA
<213> ORGANISM: Diplocladon sp.

<400> SEQUENCE: 9
atgccgaatg aaatcgtttt acatggagcc aaaccgcgag atccattaga cctgggaact     60
gcaggaagtc aattatttag gtctttgacg caattttctt atttaagaga agctctggta    120
agtgtttaac gaaaatagac aatgtacaca tcatttgaaa atattgttga aaatgggtg     180 tttttttata attttgtcta agaaaactta tatgcagttt cttaataatg ataaagtgca    240
actctttgga ttacagtctt aaagcatata attattctga gttaattttta acatattta    300 ctgtaactat aaaaaatcac tagcatttga ctggttacta tatttgaaga tacaatgcta    360
aagttaggca acccaaataa cacttttct agtttggttc gacacaatat tatttaaaag    420
atcacctata taccgatga atagaagaga aactatgatg tatgtattat acatgcaaa     480 aataatgttc ctcgttcgaa ttggaatttt tataaaatta ttaaaattc caattgatca    540 tcatatccat catatttgca aaaatatcaa cattaaaaca ttttaggtcg acgctcatac    600
tgagcaagtg gtatcttacg cggatatctt agaaaacagt tgccgtctag ctatatgctt    660
tgagaaatat ggattacgcc aaaatagtgt catagcagta tgcagcgaaa atagcgcgat    720 cttttttctac cccgtaatcg ccgctttata tatgggtatc ataacagcaa cagtaaatga    780
taactacacc gaaagtaagt ggaaaactta caaacatttt ttaatcctcc atcatatcga    840
tataatcttc caggggaatt attcgacact ttaaatattt cgaaacctga actggtattc    900
tgttcgaaga aggcgattaa aaacttgacg caattgaaga atcacatcga ttttattaaa    960
aagctcgtag ttttggatag tgatgaagac ataggtgaag tcgaatctct tgccaacttt   1020
atgaaacgct attcagaatc tgttattgat gtgagaaact ttaagcctcg cgattttgat   1080
gctaaagaac aagttgcctt aatcatgtcg tcatcaggaa caactggatt acctaaagga   1140
gtcgttctaa cccatagaaa tttgagcgtt cgctttgtac attgcaagta ggtaacagga   1200
aaaaatttgt tttgaaacta tacctaagat tgattgtacg ttattaatca aaaatccatg   1260
cgcctatatt acatggtaaa gtaggatgtg acacaactgt gtgaaacgtc atcatctact   1320 agcttttat tgatgacgta catgttgaaa taaaatttga atggcttata ccttacctta    1380
gcccaccaca ttttacctcc atttctttgc ccctagctga cagatccact tccacatcgt   1440
ttaatcctct tttcagccga tcctgaattc gaattcaaat tcgaattctc ttcttctaga   1500
agagaatttt tctctctttc cctctttttt ctatcttctc tagaaaagaa ttctagaatt   1560
```

```
ctaatcctct tttcagccga taggatgccc tatcggctgc cctatctgag tccatcattt    1620
caacgatccc tagtcatctt agagtgatga agaatttcta cgatttattg ttctagtatt    1680
gttcatttac tacaaacaaa caatacaata ataaagaatt tgaactgtga attagaaata    1740
attcgttcaa ttttgcactt agtcttacca gtcagtggag ttaggttctt agccgtgtat    1800
ttttaacctc ctttaacagg tctgggtttt tatatacatt ttctaaccca atccagacgt    1860
atattcgtgc tcgttattca ttattatcct gaccaagcca atattatcc acagttatgg     1920 acaggacagg agtcctctcc tcataaactt agtgtagttt aattttcttt agggccggtc    1980
tcgccacctt ttaataaatt tatctgacaa ataacgtaca caaccggctt ctattgtaaa    2040
aaatatttac caaataagtt tgtcgctgga ataactggtt tttccggaag atttcaataa    2100
ttagattaat cttttaggga cccgttattc ggcacaagga ctgtcccttc aacttcaatt    2160
ttatctatcg ttcctttcca tcatgcgttt ggaatgttta cgacgttgtc ctattttata    2220
gtaggactca gagtcatact actaaaaaga ttcgaagaag aattttttctt aagcactatt   2280 gaaaagtaca gaattccaac tatcgttctt gcaccacccg taatggtatt cctagccaag    2340
agtccgttag tcgatcagta cgatgtgtcc agtattagag aagttgctac cggtggtgca    2400
cctgtcggca ttgaagtggc agaagctgtt gcgaaacggt atttgttttt tttttaattg    2460
ttgaagtgtt gttttataac agttaatgta caggctaaaa attaatggaa tacttcaagg    2520
atacggtcta acagagacat gttgcgccgt attaatcacc ccacgacc atgttaaaac      2580 aggttctact gggaaagtcg ccccgtacgt gcaagcgaaa gttgtagatc ttagcaccgg    2640
aaaatctcta gggccaaata aaagaggaga acttttgcttt aaaagcgaga taattatgaa   2700
aggttatttc aacaatataa aggctacgga agaggctatc gataaagaag gatggttaca    2760
ttctggagat gtcgggtatt atgatgaaga tggtcatttc tacgtagtag atcgtttaaa    2820
agaacttatc aagtacaagg gatatcaagt atgtcgattt ttatttaagt gaacgtgtat    2880
gaatttaaga ccctttatgt attttaggtt gcaccggctg aattggaatg gttgcttttg    2940
caacatccag ctatcaaaga cgccggtgtt actggcgttc ctgacgaagc tgccggagaa    3000
cttccgggtg cttgcatagt ccttgaagaa ggacatagtc ttaccgaaca agaagttatt    3060
gaatatgtag ccggtgagtt ttagtagcat ttttagtttt taatcaattg cgcatttttt    3120
tcgtagaacg tgtttctcca actaaacgta tacgtggtgg agtagttttc gttgatgata    3180
tacccaaagg agcgactgga aaactcgtca gaagtgaatt acgagaatg ctttctcaga     3240 agaaatcgaa actataa                                                   3257
```

<210> SEQ ID NO 10
<211> LENGTH: 20
<212> TYPE: DNA
<213> ORGANISM: Artificial
<220> FEATURE:
<223> OTHER INFORMATION: T7 promoter primer

<400> SEQUENCE: 10

```
taatacgact cactataggg                                                   20
```

<210> SEQ ID NO 11
<211> LENGTH: 21
<212> TYPE: DNA
<213> ORGANISM: Artificial
<220> FEATURE:
<223> OTHER INFORMATION: T7 Reverse primer

<400> SEQUENCE: 11
ctagttattg ctcagcggtg g            21

<210> SEQ ID NO 12
<211> LENGTH: 25
<212> TYPE: DNA
<213> ORGANISM: Artificial
<220> FEATURE:
<223> OTHER INFORMATION: No51(mam)-C344S primer

<400> SEQUENCE: 12
gaccgagaca tgcagcgccg tgctg           25

<210> SEQ ID NO 13
<211> LENGTH: 1632
<212> TYPE: DNA
<213> ORGANISM: Diplocladon sp.

<400> SEQUENCE: 13
atggccaacg agattgtgct gcacggcgcc aagcccaggg accctctgga tctgggcaca      60
gccggcagcc agctgttcag aagcctgacc cagttcagct acctgcgcga ggccctggtg     120
gacgcccaca ccgaacaggt ggtgtcctac gccgacatcc tggaaaacag ctgcagactg     180
gccatctgct tcgagaagta cggcctgcgg cagaacagcg tgatcgccgt gtgcagcgag     240
aacagcgcca tcttcttcta ccctgtgatc gccgccctgt acatgggcat catcaccgcc     300
accgtgaacg acaactacac cgagagagag ctgttcgaca ccctgaacat cagcaagccc     360
gagctggtgt tctgcagcaa gaaggccatc aagaatctga cccagctgaa gaaccacatc     420
gacttcatca agaaactggt ggtgctggac agcgacgagg acatcggcga ggtggaaagc     480
ctggccaact tcatgaagcg gtacagcgag tccgtgatcg acgtgcggaa cttcaagccc     540
cgggacttcg acgccaaaga acaggtggcc ctgatcatga gcagcagcgg caccaccggc     600
ctgcctaagg gcgtggtgct gacccaccgg aacctgagcg tgcgcttcgt gcactgcaag     660
gaccctctgt tcggcaccag aaccgtgccc agcaccagca tcctgagcat cgtgcccttc     720
caccacgcct tcggcatgtt caccaccctg agctacttca tcgtgggcct gagagtgatc     780
ctgctgaaga gattcgagga agagttcttc ctgagccaca tcgagaagta tcgcatcccc     840
accatcgtgc tggcccctcc cgtgatggtg ttcctggcca agagcccct ggtggatcag     900
tacgacgtgt ccagcatcag agaggtggcc accggcggag cccctgtggg aattgaagtg     960
gccgaggccg tggccaagcg gctgaagatc aacggcatcc tgcagggcta cggcctgacc    1020
gagacatgca gcgccgtgct gatcacccc cacgaccacg tgaaaaccgg cagcaccggc     1080
aaggtggccc cctatgtgca ggccaaggtg gtggacctgt ccaccggcaa gagcctgggc    1140
cccaacaagc ggggcgagct gtgcttcaag agcgagatca tcatgaaggg ctacttcaac    1200
aacatcaagg ccaccgagga agccatcgac aaagagggct ggctgcacag cggcgacgtg    1260
ggctactacg acgaggacgg ccacttctac gtggtggacc ggctgaaaga gctgatcaag    1320
tacaagggct accaggtggc acctgccgag ctggaatggc tgctgctgca gcaccccgcc    1380
atcaaggatg ccggcgtgac cggcgtgcca gatgaagctg ctggcgagct gcctggcgcc    1440
tgtatcgtgc tggaagaggg ccactccctg accgagcagg aagtgatcga gtacgtcgcc    1500
gagcgggtgt cccccaccaa gagaatcaga ggcggcgtgg tgttcgtgga cgacatccct    1560
aagggcgcca caggcaagct ggtgcgcagc gagctgcggc ggatgctgag ccagaaaaag    1620
tccaagctgt ga                                                        1632

<210> SEQ ID NO 14
<211> LENGTH: 543
<212> TYPE: PRT
<213> ORGANISM: Diplocladon sp.

<400> SEQUENCE: 14

```
Met Ala Asn Glu Ile Val Leu His Gly Ala Lys Pro Arg Asp Pro Leu
1               5                   10                  15

Asp Leu Gly Thr Ala Gly Ser Gln Leu Phe Arg Ser Leu Thr Gln Phe
            20                  25                  30

Ser Tyr Leu Arg Glu Ala Leu Val Asp Ala His Thr Glu Gln Val Val
        35                  40                  45

Ser Tyr Ala Asp Ile Leu Glu Asn Ser Cys Arg Leu Ala Ile Cys Phe
    50                  55                  60

Glu Lys Tyr Gly Leu Arg Gln Asn Ser Val Ile Ala Val Cys Ser Glu
65                  70                  75                  80

Asn Ser Ala Ile Phe Phe Tyr Pro Val Ile Ala Ala Leu Tyr Met Gly
                85                  90                  95

Ile Ile Thr Ala Thr Val Asn Asp Asn Tyr Thr Glu Arg Glu Leu Phe
            100                 105                 110

Asp Thr Leu Asn Ile Ser Lys Pro Glu Leu Val Phe Cys Ser Lys Lys
        115                 120                 125

Ala Ile Lys Asn Leu Thr Gln Leu Lys Asn His Ile Asp Phe Ile Lys
    130                 135                 140

Lys Leu Val Val Leu Asp Ser Asp Glu Asp Ile Gly Glu Val Glu Ser
145                 150                 155                 160

Leu Ala Asn Phe Met Lys Arg Tyr Ser Glu Ser Val Ile Asp Val Arg
                165                 170                 175

Asn Phe Lys Pro Arg Asp Phe Asp Ala Lys Glu Gln Val Ala Leu Ile
            180                 185                 190

Met Ser Ser Ser Gly Thr Thr Gly Leu Pro Lys Gly Val Val Leu Thr
        195                 200                 205

His Arg Asn Leu Ser Val Arg Phe Val His Cys Lys Asp Pro Leu Phe
    210                 215                 220

Gly Thr Arg Thr Val Pro Ser Thr Ser Ile Leu Ser Ile Val Pro Phe
225                 230                 235                 240

His His Ala Phe Gly Met Phe Thr Thr Leu Ser Tyr Phe Ile Val Gly
                245                 250                 255

Leu Arg Val Ile Leu Leu Lys Arg Phe Glu Glu Glu Phe Phe Leu Ser
            260                 265                 270

Thr Ile Glu Lys Tyr Arg Ile Pro Thr Ile Val Leu Ala Pro Pro Val
        275                 280                 285

Met Val Phe Leu Ala Lys Ser Pro Leu Val Asp Gln Tyr Asp Val Ser
    290                 295                 300

Ser Ile Arg Glu Val Ala Thr Gly Gly Ala Pro Val Gly Ile Glu Val
305                 310                 315                 320

Ala Glu Ala Val Ala Lys Arg Leu Lys Ile Asn Gly Ile Leu Gln Gly
                325                 330                 335

Tyr Gly Leu Thr Glu Thr Cys Ser Ala Val Leu Ile Thr Pro His Asp
            340                 345                 350

His Val Lys Thr Gly Ser Thr Gly Lys Val Ala Pro Tyr Val Gln Ala
        355                 360                 365

Lys Val Val Asp Leu Ser Thr Gly Lys Ser Leu Gly Pro Asn Lys Arg
    370                 375                 380
```

Gly Glu Leu Cys Phe Lys Ser Glu Ile Ile Met Lys Gly Tyr Phe Asn
385                 390                 395                 400

Asn Ile Lys Ala Thr Glu Glu Ala Ile Asp Lys Glu Gly Trp Leu His
            405                 410                 415

Ser Gly Asp Val Gly Tyr Tyr Asp Glu Asp Gly His Phe Tyr Val Val
            420                 425                 430

Asp Arg Leu Lys Glu Leu Ile Lys Tyr Lys Gly Tyr Gln Val Ala Pro
            435                 440                 445

Ala Glu Leu Glu Trp Leu Leu Gln His Pro Ala Ile Lys Asp Ala
450                 455                 460

Gly Val Thr Gly Val Pro Asp Glu Ala Gly Glu Leu Pro Gly Ala
465                 470                 475                 480

Cys Ile Val Leu Glu Glu Gly His Ser Leu Thr Glu Gln Val Ile
            485                 490                 495

Glu Tyr Val Ala Glu Arg Val Ser Pro Thr Lys Arg Ile Arg Gly Gly
            500                 505                 510

Val Val Phe Val Asp Asp Ile Pro Lys Gly Ala Thr Gly Lys Leu Val
            515                 520                 525

Arg Ser Glu Leu Arg Arg Met Leu Ser Gln Lys Lys Ser Lys Leu
530                 535                 540

<210> SEQ ID NO 15
<211> LENGTH: 543
<212> TYPE: PRT
<213> ORGANISM: Diplocladon sp.

<400> SEQUENCE: 15

Met Pro Asn Glu Ile Val Leu His Gly Ala Lys Pro Arg Asp Pro Leu
1               5                   10                  15

Asp Leu Gly Thr Ala Gly Ser Gln Leu Phe Arg Ser Leu Thr Gln Phe
            20                  25                  30

Ser Tyr Leu Arg Glu Ala Leu Val Asp Ala His Thr Glu Gln Val Val
        35                  40                  45

Ser Tyr Ala Asp Ile Leu Glu Asn Ser Cys Arg Leu Ala Ile Cys Phe
    50                  55                  60

Glu Lys Tyr Gly Leu Arg Gln Asn Ser Val Ile Ala Val Cys Ser Glu
65                  70                  75                  80

Asn Ser Ala Ile Phe Phe Tyr Pro Val Ile Ala Ala Leu Tyr Met Gly
                85                  90                  95

Ile Ile Thr Ala Thr Val Asn Asp Asn Tyr Thr Glu Arg Glu Leu Phe
            100                 105                 110

Asp Thr Leu Asn Ile Ser Lys Pro Glu Leu Val Phe Cys Ser Lys Lys
        115                 120                 125

Ala Ile Lys Asn Leu Thr Gln Leu Lys Asn His Ile Asp Phe Ile Lys
    130                 135                 140

Lys Leu Val Val Leu Asp Ser Asp Glu Asp Ile Gly Glu Val Glu Ser
145                 150                 155                 160

Leu Ala Asn Phe Met Lys Arg Tyr Ser Glu Ser Val Ile Asp Val Arg
                165                 170                 175

Asn Phe Lys Pro Arg Asp Phe Asp Ala Lys Glu Gln Val Ala Leu Ile
            180                 185                 190

Met Ser Ser Ser Gly Thr Thr Gly Leu Pro Lys Gly Val Val Leu Thr
        195                 200                 205

His Arg Asn Leu Ser Val Arg Phe Val His Cys Lys Asp Pro Leu Phe

-continued

```
            210                 215                 220

Gly Thr Arg Thr Val Pro Ser Thr Ser Ile Leu Ser Ile Val Pro Phe
225                 230                 235                 240

His His Ala Phe Gly Met Phe Thr Thr Leu Ser Tyr Phe Ile Val Gly
                245                 250                 255

Leu Arg Val Ile Leu Leu Lys Arg Phe Glu Glu Phe Phe Leu Ser
                260                 265                 270

Thr Ile Glu Lys Tyr Arg Ile Pro Thr Ile Val Leu Ala Pro Pro Val
                275                 280                 285

Met Val Phe Leu Ala Lys Ser Pro Leu Val Asp Gln Tyr Asp Val Ser
                290                 295                 300

Ser Ile Arg Glu Val Ala Thr Gly Gly Ala Pro Val Gly Ile Glu Val
305                 310                 315                 320

Ala Glu Ala Val Ala Lys Arg Leu Lys Ile Asn Gly Ile Leu Gln Gly
                325                 330                 335

Tyr Gly Leu Thr Glu Thr Cys Ser Ala Val Leu Ile Thr Pro His Asp
                340                 345                 350

His Val Lys Thr Gly Ser Thr Gly Lys Val Ala Pro Tyr Val Gln Ala
                355                 360                 365

Lys Val Val Asp Leu Ser Thr Gly Lys Ser Leu Gly Pro Asn Lys Arg
                370                 375                 380

Gly Glu Leu Cys Phe Lys Ser Glu Ile Ile Met Lys Gly Tyr Phe Asn
385                 390                 395                 400

Asn Ile Lys Ala Thr Glu Glu Ala Ile Asp Lys Glu Gly Trp Leu His
                405                 410                 415

Ser Gly Asp Val Gly Tyr Tyr Asp Glu Asp Gly His Phe Tyr Val Val
                420                 425                 430

Asp Arg Leu Lys Glu Leu Ile Lys Tyr Lys Gly Tyr Gln Val Ala Pro
                435                 440                 445

Ala Glu Leu Glu Trp Leu Leu Leu Gln His Pro Ala Ile Lys Asp Ala
450                 455                 460

Gly Val Thr Gly Val Pro Asp Glu Ala Ala Gly Glu Leu Pro Gly Ala
465                 470                 475                 480

Cys Ile Val Leu Glu Glu Gly His Ser Leu Thr Glu Gln Glu Val Ile
                485                 490                 495

Glu Tyr Val Ala Glu Arg Val Ser Pro Thr Lys Arg Ile Arg Gly Gly
                500                 505                 510

Val Val Phe Val Asp Asp Ile Pro Lys Gly Ala Thr Gly Lys Leu Val
                515                 520                 525

Arg Ser Glu Leu Arg Arg Met Leu Ser Gln Lys Lys Ser Lys Leu
530                 535                 540
```

STAR-WORM LUCIFERASE

CROSS REFERENCE TO RELATED APPLICATIONS

This application is a Continuation application of PCT Application No. PCT/JP2012/056802, filed Mar. 12, 2012 and based upon and claiming the benefit of priority from prior Malaysian Patent Application No. PI2011001154, filed Mar. 15, 2011, the entire contents of all of which are incorporated herein by reference.

INCORPORATION BY REFERENCE OF SEQUENCE LISTING

The Sequence Listing in an ASCII text file, named as SequenceListing.txt of 26.0 KB, created on Nov. 13, 2013, and submitted to the United States Patent and Trademark Office via EFS-Web, is incorporated herein by reference.

BACKGROUND OF THE INVENTION

1. Field of the Invention

The present invention relates to a luciferase of luminous insect star-worm which belongs to Arthropoda phylum, Insecta class, Coleoptera order. More specifically, it relates to a luciferase cloned from a star-worm and to a mutant thereof, and to a method for determining function of a cell by expressing a gene of the luciferase in a cell and detecting luminescence by means of imaging.

2. Description of the Related Art

For determining function of cells such as intracellular signal transduction and gene expression, a fluorescent probe such as a fluorescent dye and fluorescent protein and a luminescence probe utilizing a luciferine-luciferase reaction have been used. Especially, for the analysis of gene expression regulation, luminescence measurement is used, which does not cause damage of cell due to exciton light or a problem of autoluminescence and is excellent in terms of quantitative determination. For example, in the case of observing a cell into which a luciferase gene is introduced, the intensity of expression of the luciferase gene (more specifically, the expression amount) can be determined by measuring luminescence from the cell by luciferase. The measurement of degree of the luminescence is performed by the procedures in which luciferine, Adenosine triphosphate (ATP), and the like are added to lysate prepared by lysis of cells, and the lysate is subjected to a quantitative determination by a luminometer utilizing a photoelectric multiplier. Namely, luminescence is measured after lysis of cells, and thus the expression amount of the luciferase gene at a certain time point is determined as an average value of the entire cell. Examples of a method for introducing a luminescent gene such as luciferase gene as a reporter gene are a calcium phosphate method, lipofection method, and electroporation method, and each of these methods is used depending on the purpose and type of cells. Analysis of the expression amount of luciferase with use of an objective DNA fragment ligated to the upstream or downstream of a luciferase gene to be introduced into a cell enables study of the effect of the DNA fragment on luciferase gene transcription. Further, co-expression of a luciferase gene to be introduced into a cell and the objective gene enables study of the effect of the gene product on luciferase gene expression.

For time-course analysis of the expression amount of a luminescent gene, the degree of luminescence of a living cell needs to be measured over time. Such measurement is carried out by cell cultivation in an incubator provided with a luminometer and quantitative determination of the degree of luminescence from the whole cell population at regular time intervals. Consequently, for example, an expression rhythm having a certain cycle can be analyzed, and temporal change of the expression amount of the luminescent gene in the entire cell can be obtained.

In recent years, in a field of biology and medical science there is increasing necessity of the time course observation of dynamic alterations in living samples with images. In a field of utilizing observation of fluorescence, time lapse or dynamic image pickup has been adopted for understanding function of a protein molecular dynamically. In the conventional technique, time course observation with use of a fluorescent sample has been carried out, for example, observation of moving images for one molecule of a protein provided with an added fluorescent molecule.

In contrast, when a luminescent sample is used for time-course observation, use of a CCD camera equipped with an image intensifier is required since the luminous intensity of the luminescent sample is extremely low. Recently, a microscope equipped with an optical system for observation of luminescent samples has been developed (Jpn. Pat. Appln. KOKAI Publication No. 2006-301599, International Publication No. 2006/088109).

Upon image pickup of a luminescent sample having small luminous intensity, it should be exposed for a longer term for obtaining clear image. Such a luminescent sample is used for only limited research. For example, when 30 minutes of exposure is required because of low luminous intensity, time-course image pickup is possible at every 30 minutes but is not at a shorter time interval, and real-time image pickup is also impossible. Upon acquisition of images, plural images should be obtained and compared in order to focus on cells which emit light, and thus it is time-consuming when longer exposure time is required because of low luminous intensity.

BRIEF SUMMARY OF THE INVENTION

The object of the present invention is to provide a luciferase which enables easier measurement or observation in comparison to a conventional luciferase.

According to the first aspect of the present invention, there is provided a luciferase derived from a star-worm belonging to the genus *Diplocladon*.

According to the second aspect of the present invention, there is provided a luciferase which induces luminescence such that a maximum luminous wavelength falls within a range of 557 to 562 nm over the entire pH range of 5.5 to 8.0.

According to the third aspect of the present invention, there is provided a luciferase which induces luminescence having 1.5 times the luminous intensity of luminescence induced by a known luciferase from *Photinus pylalis* firefly in a mammalian cell.

According to the fourth aspect of the present invention, there is provided a luciferase which induces luminescence such that a change of a maximum luminous wavelength is small when pH varies, thereby measurement or observation can be carried out by reducing an influence by pH of an environment. According to a further aspect of the present invention, there is provided a luciferase which induces luminescence having 1.5 times the luminous intensity of that induced by a known firefly luciferase, thereby reducing exposure time for luminescent image pickup, and enabling time-course observation with higher time resolution in comparison to that of the conventional technique.

BRIEF DESCRIPTION OF THE SEVERAL VIEWS OF THE DRAWING

FIG. 2 illustrates Km values of various luciferases.

DETAILED DESCRIPTION OF THE INVENTION

Figure 1:
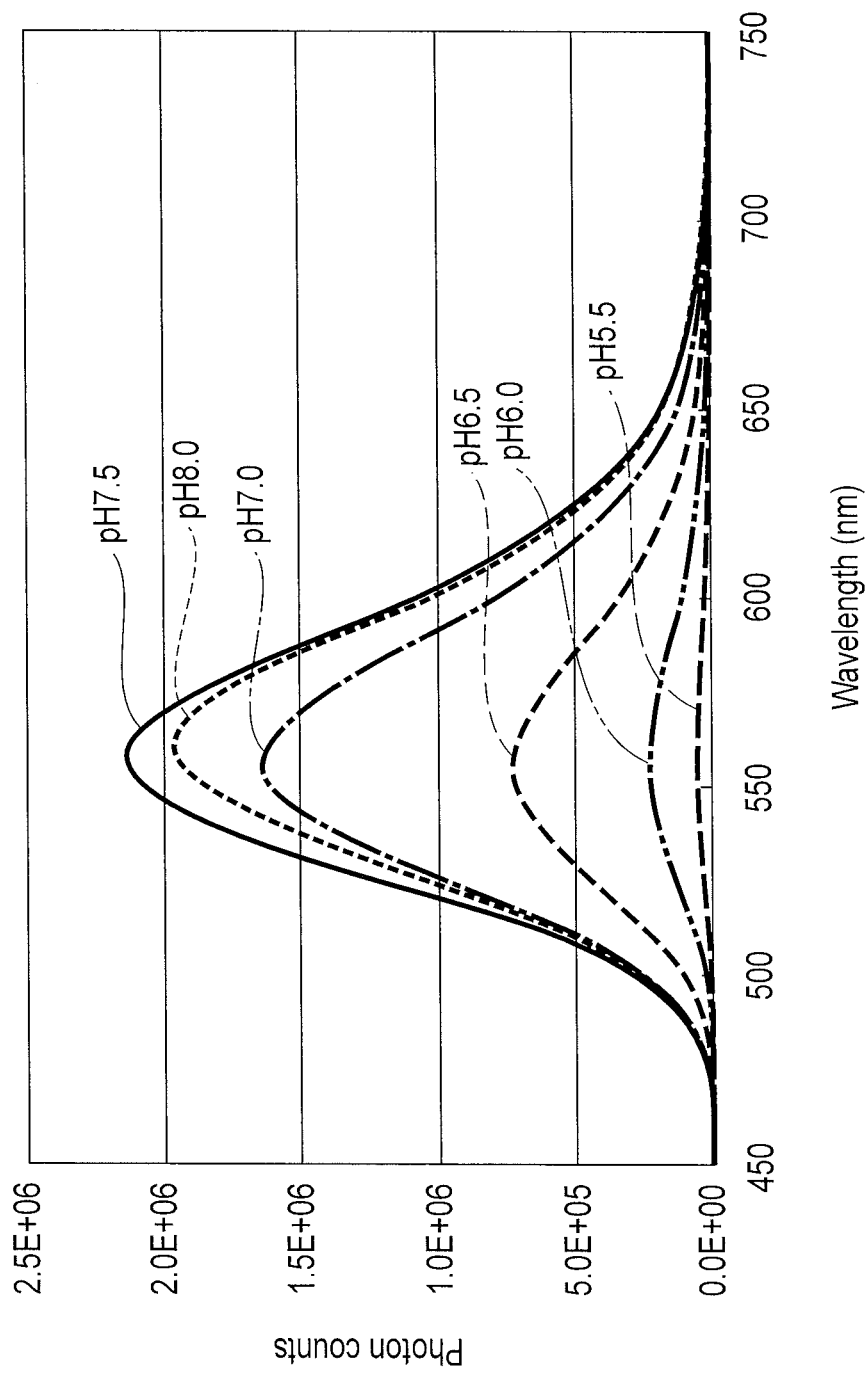
FIG. 1 shows emission spectra of a star-worm luciferase at various pHs.

An embodiment of the present invention relates to luciferase derived from a star-worm belonging to the genus *Diplocladon*.

"Luciferase" is a class of enzyme which catalyzes a luminescent chemical reaction. The substrate of this enzyme is called as luciferin. In the presence of ATP, light emission occurs upon chemical reaction of luciferin because of the catalytic activity of luciferase. Presently, luciferases derived from fireflies and bacteria have been obtained. The luciferase of an embodiment also has the same meaning indicated above, but is novel in the point that it has been first obtained from the star-worm described below. Here, the term "derive" includes not only a wild-type luciferase from a star-worm but also a mutant thereof.

"Star-worm" is an insect belonging to Arthropoda phylum, Insecta class, Coleoptera order, Phengodidae family, *Diplocladon* genus. A star-worm has been confirmed to be native mainly to South Asia, Southeast Asia, and East Asia. A railroad worm belonging to Phengodidae family, *Phrixothrix* genus, which is closely related to the genus *Diplocladon*, is native to South and Central America.

A luciferase of an embodiment of the present invention is, for example, those containing amino acid sequence represented by SEQ ID NO: 1. The luciferase is obtained from a star-worm. In the specification and claims attached thereto, the luciferase is referred to as, for example, a star-worm luciferase and a star-worm derived luciferase.

The luciferase of an embodiment of the present invention has a characteristic of inducing luminescence such that change of a maximum luminous wavelength is small when pH varies. Here, "maximum luminous wavelength" means a wavelength at which intensity of luminescence is the maximum within a measurement wavelength range in a luminous reaction in which a luciferase is involved. With use of said luciferase a measurement or observation can be carried out, reducing an environmental pH influence. For example, with respect to luminescence induced by luciferases which are present in an environment of different pHs, luminous intensities can be measured at a single wavelength at the same time in an imaging by microscope. According to the luciferase of an embodiment of the present invention, quantitative measurement can be facilitated even with use of an apparatus in which photoelectric conversion efficiency varies depending on the measurement wavelength, for example, CCD. When a measurement is carried out with use of a conventional luciferase, the measurement wavelength needs be adjusted for each pH, which makes quantitative comparison difficult due to the difference of measurement wavelength. In contrast, when a measurement is carried out with use of a luciferase of an embodiment of the present invention, a single measurement wavelength can be used thereby making quantitative comparison easier.

A luciferase of an embodiment of the present invention is characterized by inducing luminescence such that a maximum luminous wavelength falls within a certain range over a certain pH range. For example, a luciferase of an embodiment of the present invention induces luminescence such that a maximum luminous wavelength falls within a range of 520-600 nm, 530-590 nm, 540-580 nm, 545-575 nm, 550-570 nm, 555-565 nm or 557-562 nm over the entire range of pH 6.5-7.0, pH 6.0-7.5, pH 5.5-8.0, pH 5.0-8.5 or pH 4.5-9.0.

A luciferase of an embodiment of the present invention is characterized in that change of a maximum luminous wavelength falls within a certain value when pH varies over a certain range. For example, according to a luciferase of an embodiment of the present invention, change of the maximum luminous wavelength falls within 80, 60, 40, 30, 20, 10 or 5 nm when pH varies over a range of pH 6.5-7.0, pH 6.0-7.5, pH 5.5-8.0, pH 5.0-8.5 or pH 4.5-9.0.

FIG. 1 shows luminescence spectra of luminescence induced by a luciferase of an embodiment of the present invention. As shown by the figure, the luciferase induces luminescence having a maximum luminous wavelength which falls within a range of 557-562 nm over the entire range of pH 5.5-8.0. Within the range of pH 5.5-8.0, the change of the maximum luminous wavelength falls within 5 nm.

A luciferase of an embodiment of the present invention induces luminescence with higher intensity in comparison to the intensity of luminescence induced by a known luciferase. Therefore, a luciferase of an embodiment exhibits particularly advantageous effect when it is utilized as a reporter for imaging a protein. Namely, a luciferase of an embodiment can provide high luminous intensity even in a small amount, and thus excellent detection can be achieved with respect to a protein with a small expression amount. Further, a luciferase of an embodiment enables reduction of the exposure time which is necessary for detection owing to the high luminous intensity. Therefore, the interval between image pickups can be shorten by utilizing a luciferase of an embodiment of the present invention as a reporter for time-course observation, thereby achieving observation which is closer to real-time observation.

Figure 3:
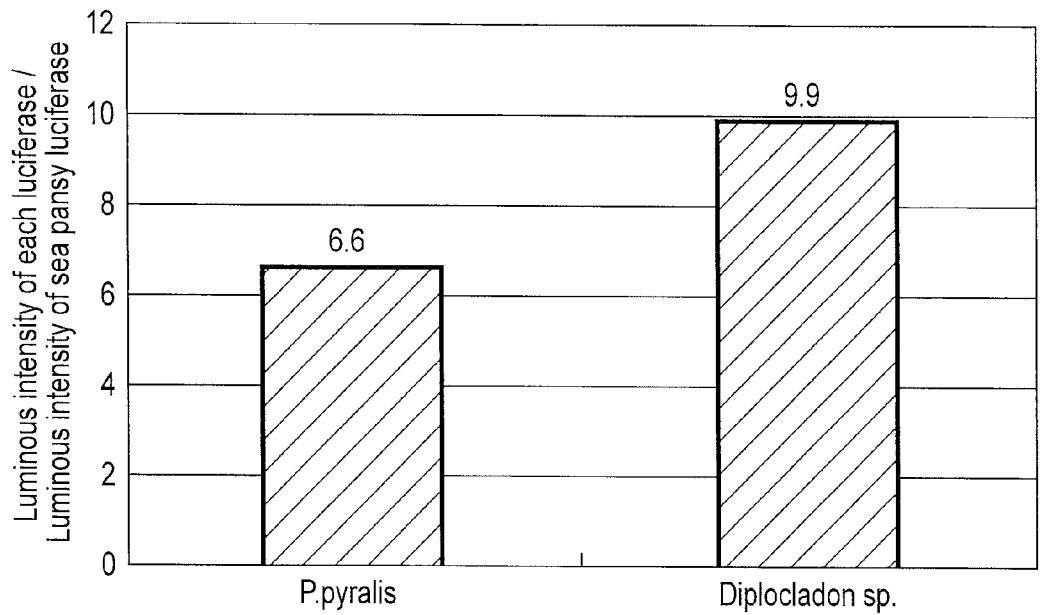
FIG. 3 compares luminous intensity between a star-worm luciferase and *Photonus pylalis* firefly luciferase, which were expressed in a mammalian cell.

In FIG. 3, luminous intensity is compared between a star-worm luciferase of an embodiment of the present invention and *P. pyralis* firefly luciferase. As shown by the figure, the star-worm luciferase can induce luminescence having 1.5 times the luminous intensity of that induced by *P. pyralis* firefly luciferase.

A luciferase of an embodiment of the present invention includes not only a wild type luciferase which is derived from a star-worm, but also a mutant luciferase in which a part of the amino acid sequence of the wild-type luciferase is mutated. Such mutation may be those which improve the enzymatic activity thereof. Such mutation may be those which improve experimental operability thereof. For example, when a wild-type luciferase indicates a low solubility in a mammalian cell, a mutant luciferase of an embodiment of the present invention may be those into which mutation is introduced for increasing the solubility thereof. Here, a mutant luciferase may be those which contains mutation in the amino acid sequence, for example, substitution, deletion, and/or addition of amino acids, as long as it exhibits the characteristics of a luciferase of an embodiment of the present invention, that is, higher luminous intensity in comparison to conventional luciferases. The mutation is those of at least one of amino acid sequence of the wild-type luciferase, and preferably those of from 1 to 20, from 1 to 15, from 1 to 10, or 1 to 5 amino acids of the wild-type luciferase. Preferably, amino acid sequence of a mutant luciferase has homology of 75% or more, 80% or more, 85% or more, 90% or more, 95% or more, 96% or more, 97% or more, 98% or more, or 99% or more with amino acid sequence of the wild-type luciferase.

Figure 4:
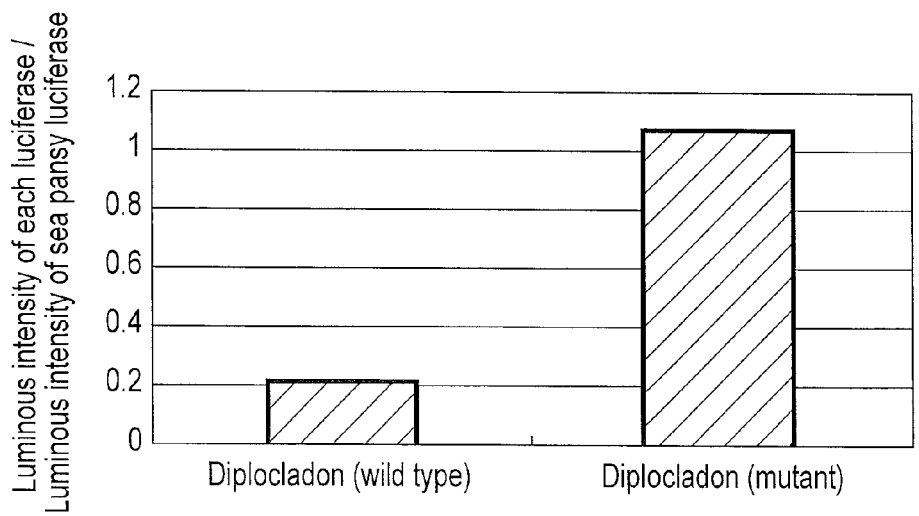
FIG. 4 compares luminous intensity between a star-worm wild-type luciferase and star-worm mutant luciferase, which were expressed in a mammalian cell.

An example of such a mutant star-worm luciferase is a luciferase having the amino acid sequence represented by SEQ ID NO: 15. The mutant luciferase is a luciferase in which cysteine at position 344 in the amino acid sequence of SEQ ID NO: 1 is substituted by serine. The mutant luciferase induces luminescence having higher luminous intensity in comparison to a star-worm wild type luciferase. FIG. 4 compares luminous intensity between the star-worm mutant luciferase and the star-worm wild type luciferase. The star-worm mutant luciferase induces luminescence having 4.9 times the luminous intensity of that induced by the star-worm wild-type luciferase.

The present invention relates to a nucleic acid containing base sequence which encodes a luciferase of an embodiment of the present invention. Namely, the nucleic acid contains a luciferase gene which is derived from a star-worm. A nucleic acid means, for example, DNA or RNA. A "gene" of a luciferase means mainly a region transcribed by mRNA, that is, it means a structural gene.

A nucleic acid containing base sequence which encodes a luciferase of an embodiment is those containing base sequence represented by SEQ ID NO: 2. A gene having this sequence is cloned from a star-worm and encodes a star-worm wild-type luciferase.

The nucleic acid of an embodiment may be those containing base sequence of a wild-type luciferase gene and those containing base sequence of a mutant luciferase gene having a mutation therein. Here, the mutant luciferase gene may be a gene in which a specific base in the base sequence, for example, several bases are substituted, deleted, and/or added, as long as it can exhibit the characteristics of a luciferase of one embodiment. Mutation of base sequence includes those which do not cause alteration of the amino acid sequence to be encoded. Namely, a nucleic acid of an embodiment includes those containing a mutated luciferase gene which encodes a wild-type luciferase.

An example of mutation which does not cause alternation of the amino acid sequence to be encoded is those which cancel recognition sequence of a specific restriction enzyme. Because of this mutation, the nucleic acid containing the gene is not digested by the restriction enzyme, but the gene can encode the protein having the same amino acid sequence as that of before mutation. Such mutation can be achieved by converting the codons constituting the recognition sequence of the restriction enzyme to the synonymous codons. Such mutation is useful when the recognition sequence of the restriction enzyme to be used for genetic recombination is included in the gene. In this case, fragmentation of the nucleic acid upon treatment of a restriction enzyme can be prevented by canceling the recognition sequence of the gene in advance, thereby facilitating genetic recombination.

Another example of mutation which does not cause alteration of an amino acid to be coded is those which optimizes codons of a gene for expression in a specific organism species. Here, the term "optimization" means to substitute codons of a gene contained in a nucleic acid by codons which has high codon frequency in a specific organism species. If the optimization is carried out, expression of a gene in a specific organism species is enhanced in comparison to the case without optimization. A luciferase gene of an embodiment is derived from a star-worm, and therefore, as the organism species to which the gene is introduced is farther from a star-worm in terms of taxonomy, the higher effects can be obtained by optimization. A specific organism species is, for example, a bacterial cell, yeast cell, and mammalian cell. A mammalian cell is, for example, a mouse cell, monkey cell, and human cell.

A nucleic acid of an embodiment containing base sequence which encodes a luciferase in which a codon is optimized is, for example, those containing base sequence represented by SEQ ID NO: 3. In the nucleic acid, the recognition sequences of BamHI and EcoRI are cancelled and a codon is optimized for expression in a mammalian cell.

A nucleic acid of an embodiment of the present invention is, for example, those containing a luciferase gene provided with Kozak sequence. Kozak sequence is sequence comprised of initiation codon and plural base sequences located in before and after the initiation codon. It has been proved that an expression amount of a gene is increased because of presence of Kozak sequence. With respect to Kozak sequence, common sequence has been found in each organism species or biome. A nucleic acid containing Kozak sequence of an embodiment has Kozak sequence corresponding to the organism species to which it is introduced. For example, in the case where it is introduced into a mammalian cell, the nucleic acid contains SEQ ID NO: 4 as Kozak sequence, in which r means guanine or adenine. The amino acid which is immediately after the initiation codon can be changed according to addition of Kozak sequence. A luciferase gene to be provided with Kozak sequence may be a wild-type gene and mutant gene in which codons are optimized in such a manner described above.

The present invention includes a vector containing these nucleic acids. The vector may contain a nucleic acid containing sequence for regulating expression or sequence of a marker gene other than the nucleic acid encoding luciferase, and the like.

The present invention relates to a method for analyzing function in a cell by utilizing a luciferase of an embodiment. The method includes introducing the luciferase of the embodiment into a cell and detecting luminescence of the luciferase with an imaging apparatus. For example, a luciferase gene of an embodiment introduced in downstream of a specific expression regulation region in DNA, and the expression of luciferase is detected based on the presence or absence of luminescence, thereby enabling study of the function of the expression regulation region.

The present invention relates to a method for analyzing an intracellular protein utilizing a luciferase of an embodiment. The method includes introducing a fusion protein comprised of a luciferase of an embodiment and a protein to be analyzed, and detecting luminescence of the luciferase with an imaging apparatus.

The method includes observation of localization of a protein to be analyzed in a cell and time-course observation (time-lapse) of the localization. The method includes confirmation not only of protein localization but also of mere expression. A cell to be used is nonexclusive, and may be those which can be ordinarily used in a field of cell imaging. Further, a protein to be analyzed is also nonexclusive, and it can be selected in accordance with the aim of research. The protein may be those which essentially exist in a cell to be used, or may be a heterogeneous or modified protein which does not essentially exist in a cell.

Upon introducing a fusion protein into a cell, a known introduction method can be applied. One of them is a method for directly introducing a fusion protein purified in vitro into a cell. For example, a fusion protein can be directly injected into a cell by a microinjection method. Or, a cell is incubated in culture medium containing a fusion protein, thereby causing uptake of the fusion protein into a cell by endocytosis.

Another method is to introduce a nucleic acid containing the base sequence encoding the fusion protein to express the fusion protein in a cell. For example, an expression vector containing the nucleic acid is introduced into a cell by a calcium phosphate method, lipofection, electroporation, and the like, thereby enabling expression of the fusion protein from the expression vector. Here, a gene of a fusion protein contains a luciferase gene of an embodiment of the present invention and a gene of a protein to be analyzed, in which the luciferase gene and the gene of the protein are linked in such a manner that each of them can be normally translated.

Upon detection of luminescence by luciferase with an imaging apparatus, a well known detection method can be applied. For example, a luciferase luminous reaction is caused by adding luciferin, ATP, $Mg^{2+}$ ions, and the like to a cell which expresses a fusion protein containing luciferase as appropriate, and the generated luminescence can be detected by an imaging apparatus. The imaging apparatus is, for example, a microscope provided with a filter for capturing luminescence. The protein localization can be specified by using a microscope based on information obtained through identification of luminous position in a cell. As an imaging apparatus, a microscope provided with function which enables time-course image pickup can be used, and time-course observation can be achieved by the microscope.

Example 1

Cloning of Luciferase Gene

1. Material

Female imaginal star-worms collected in the state of Perak, Malaysia were used as a material. The star-worms have been proved to belong to the genus *Diplocladon*, but a scientific name has not been assigned thereto. In this disclosure, the species is referred to as *Diplocladon* sp. 1.

2. Extraction of Total RNA

Tissue pieces were cut off from around an abdominal portion of female imaginal *Diplocladon* sp. 1 by a scissor. Total DNA extraction was carried out from the tissue pieces with use of DNeasy Blood & Tissue Kit (QIAGEN) according to the manual thereof. The obtained total DNA was subjected to luciferase gene amplification experiments as total DNA derived from *Diplocladon* sp. 1.

3. Identification of a Star-Worm Luciferase 3-1. PCR with Use of Total DNA as a Template Specific primers were designed for PCR which amplifies a star-worm luciferase gene containing introns with use of total DNA as a template. The primers are Home-Diplo(I)-BamHI-F (SEQ ID NO:5) and Home-Diplo(I)-stop-EcoRI-R (SEQ ID NO:6). Synthesis of these primers was commissioned to Life Technologies, Japan, Co., Ltd.

To 19 µl of PCR reaction solution containing 10×Ex Taq Buffer diluted tenfold (20 mM $Mg^{2+}$ plus), dNTP Mixture at a final concentration of 0.2 mM (2.5 mL for each base), TaKaRa Ex Taq (5 U/µl) at a final concentration of 0.05 U/µl, and primers of SEQ ID NOS: 5 and 6 at a final concentration of 0.3 µM, added was 1.0 µl of a star-worm total DNA solution. Here, a concentration of the star-worm total DNA solution was not determined. In the PCR reaction, the obtained solution was thermally denatured for 2 minutes at 94° C., and then the cycle consisting of 30 seconds at 94° C., 30 seconds at 50° C., and 2 minutes at 72° C. was repeated 35 times, followed by an elongation reaction at 72° C. for 5 minutes.

3-2. Determination of Base Sequence of the Gene Amplified by PCR with Use of Total DNA as a Template In order to determine the base sequence of the gene amplified by PCR with use of total DNA, purification, subcloning, and direct sequencing of the PCR products were carried out. The details are described below.

The aimed gene fragments were collected by means of gel extraction. The gel extraction was carried out with use of Wizard SV Gel and PCR Clean-UP System (Promega KK) according to the manual thereof. Subcloning of the PCR products extracted from gel were carried out by means of TA cloning. TA cloning was carried out with use of pGEM-T Easy Vector System (Promega KK) according to the manual thereof.

Subsequently, the vector DNA was transformed to *Escherichia coli* (TOP10 strain or DH5α strain), and insert-positive colonies were selected by means of blue-white screening. The selected colonies were subjected to a direct colony PCR, and confirmed that the objective gene was inserted. In a direct colony PCR, a primer pair consisting of M13-F(−29) Primer (5'-CAC GAC GTT GTA AAA CGA C-3': SEQ ID NO: 7) and M13 Reverse (5'-GGA TAA CAA TTT CAC AGG-3': SEQ ID NO: 8) was used. To 10 µl of PCR reaction solution comprising 10×Ex Taq Buffer (20 mM $Mg^{2+}$ plus) diluted tenfold, dNTP Mixture at a final concentration of 0.2 mM (2.5 mL for each base), TaKaRa Ex Taq (5 U/µl) at a final concentration of 0.05 U/µl, and a primer pair at a final concentration of 0.2 µM, added was a small amount of colony of *Escherichia coli*. In the PCR reaction, the solution was thermally denatured for 1 minute at 94° C., and then the cycle consisting of 30 seconds at 94° C., 30 seconds at 50° C., and 2 minutes at 72° C. was repeated 25 times, followed by an elongation reaction at 72° C. for 2 minutes. After the PCR reaction, 2 µl of a PCR reaction solution was applied to 1% tris acetic acid buffer (TAE) agarose gel electrophoresis, and observed bands of the amplified genes under exposure of ultraviolet after dyeing with ethidium bromide.

With regard to the PCR reaction solution for which amplification was confirmed, the base sequence of the gene was determined by means of a direct sequencing method. With use of PCR product purification kit EXoSAP-IT (GE Healthcare Bioscience), the extra dNTP and primers contained in the PCR reaction solution was removed, and a template for the PCR direct sequencing was prepared. With use of BigDye Terminator v3.1 Cycle Sequencing Kit (Applied Biosystems), a sequencing reaction solution containing the template was prepared, and a sequencing reaction was performed with use of a thermal cycler. Purification and sequencing of the PCR products were each carried according to the manuals thereof. After the sequencing reaction, the reaction products were purified as described below. 100% ethanol of 2.5 times of weight was added to the reaction solution, and then a nucleic acid was precipitated by a centrifuge. After the supernatant was removed, the precipitate was washed by adding 70% ethanol, followed by precipitation by a centrifuge. Finally after the supernatant was removed, the precipitate was dried. To the purified precipitate, 15 µl of Hi-Di Formamide (Applied Biosystems) was added and dissolved. The solution was subjected to thermal denaturation at 94° C. for 2 minutes, and further rapidly cooled on ice, thereby providing a sample for determination of base sequence. With respect to the sample, the base sequence was determined by using Applied Biosystems 3130x1 genetic analyzer (Applied Biosystems). The analytical method was carried out according to the manual.

The obtained gene sequence was analyzed by the "sequence linking" function of sequence information analysis software DNASIS Pro. With respect to the sequence, homology research was performed by using blastx search provided by the National Center for Biotechnology Information (NCBI), and it was confirmed that the sequence indicates a high homology with base sequences of known firefly luciferases. The obtained base sequence (SEQ ID NO: 9) contains five introns, and the base sequence (SEQ ID NO: 2) from which these introns were removed was translated into amino acid sequence. The translated amino acid sequence was used as amino acid sequence of a novel star-worm luciferase (SEQ ID NO: 1). The base sequence obtained by the aforementioned experiments and analysis was determined as a novel star-worm luciferase gene.

The sequences represented by NOS: 1, 2, and 9 are indicated below.

SEQ ID NO: 1
MPNEIVLHGAKPRDPLDLGTAGSQLFRSLTQFSYLREALVDAHTEQVVS
YADILENSCRLAICFEKYGLRQNSVIAVCSENSAIFFYPVIAALYMGII
TATVNDNYTERELFDTLNISKPELVFCSKKAIKNLTQLKNHIDFIKKLV
VLDSDEDIGEVESLANFMKRYSESVIDVRNFKPRDFDAKEQVALIMSSS
GTTGLPKGVVLTHRNLSVRFVHCKDPLFGTRTVPSTSILSIVPFHHAFG
MFTTLSYFIVGLRVILLKRFEEEFFLSTIEKYRIPTIVLAPPVMVFLAK
SPLVDQYDVSSIREVATGGAPVGIEVAEAVAKRLKINGILQGYGLTETC
CAVLITPHDHVKTGSTGKVAPYVQAKVVDLSTGKSLGPNKRGELCFKSE
IIMKGYFNNIKATEEAIDKEGWLHSGDVGYYDEDGHFYVVDRLKELIKY
KGYQVAPAELEWLLLQHPAIKDAGVTGVPDEAAGELPGACIVLEEGHSL
TEQEVIEYVAERVSPTKRIRGGVVFVDDIPKGATGKLVRSELRRMLSQK
KSKL

SEQ ID NO: 2
atgccgaatgaaatcgttttacatggagccaaaccgcgagatccattag
acctgggaactgcaggaagtcaattatttaggtcttttgacgcaattttc
ttatttaagagaagctctggtcgacgctcatactgagcaagtggtatct
tacgcggatatcttagaaaacagttgccgtctagctatatgctttgaga
atatgattacgccaaaatagtgtcatagcagtatgcagcgaaaatag
cgcgatcttttctaccccgtaatcgccgctttatatatgggtatcata
acagcaacagtaaatgataactacaccgaaagggaattattcgacactt
taaatatttcgaaacctgaactggtattctgttcgaagaaggcgattaa
aaacttgacgcaattgaagaatcacatcgatttattaaaaagctcgta
gttttggatagtgatgaagacataggtgaagtcgaatctcttgccaact
ttatgaaacgctattcagaatctgttattgatgtgagaaactttaagcc
tcgcgattttgatgctaaagaacaagttgccttaatcatgtcgtcatca
ggaacaactggattacctaaaggagtcgttctaacccatagaaatttga
gcgttcgctttgtacattgcaaggacccgttattcggcacaaggactgt
cccttcaacttcaattttatctatcgttcctttccatcatgcgtttgga
atgtttacgacgttgtcctattttatagtaggactcagagtcatactac
taaaaagattcgaagaagaattttcttaagcactattgaaaagtacag
aattccaactatcgttcttgcaccaccgtaatggtattcctagccaag
agtccgttagtcgatcagtacgatgtgtccagtattagagaagttgcta ccggtggtgcacctgtcggcattgaagtggcagaagctgttgcgaaacg
gctaaaaattaatggaatacttcaaggatacggtctaacagagacatgt
tgcgccgtattaatcacccacacgaccatgttaaaacaggttctactg
ggaaagtcgccccgtacgtgcaagcgaaagttgtagatcttagcaccgg
aaaatctctagggccaaataaaagaggagaactttgctttaaaagcgag
cataattatgaaaggttatttcaacaatataaaggtacggaagaggcta
tcgataaagaaggatggttacattctggagatgtcgggtattatgatga
agatggtcatttctacgtagtagatcgtttaaaagaacttatcaagtac
aagggatatcaagttgcaccggctgaattggaatggttgcttttgcaac
atccagctatcaaagacgccggtgttactggcgttcctgacgaagctgc
cggagaacttccgggtgcttgcatagtccttgaagaaggacatagtctt
accgaacaagaagttattgaatatgtagccgaacgtgtttctccaacta
aacgtatacgtggtggagtagttttcgttgatgatatacccaaaggagc
gactggaaaactcgtcagaagtgaattacggagaatgctttctcagaag
aaatcgaaactataa SEQ ID NO: 9
atgccgaatgaaatcgttttacatggagccaaaccgcgagatccattag
acctgggaactgcaggaagtcaattatttaggtcttttgacgcaattttc
ttatttaagagaagctctggtaagtgtttaacgaaaatagacaatgtac
acatcatttgaaaatattgttgaaaaatgggtgttttttttataattttg
tctaaagaaacttatatgcagtttcttaataatgataaagtgcaactct
ttggattacagtcttaaagcatataattattctgagttaattttaacat
attttactgtaactataaaaaatcactagcatttgactggttactatat
ttgaagatacaatgctaaagttaggcaacccaaataacacttttttctag
tttggttcgacacaatattattttaaaagatcacctatatataccgatga
tagaagagaaactatgatgtatgtattattacatgcaaaaataatgttc
ctcgttcgaattggaattttttataaaattaattaaaattccaattgatc
atcatatccatcatatttgcaaaaatatcaacattaaaacattttaggt
cgacgctcatactgagcaagtggtatcttacgcggatatcttagaaaac
agttgccgtctagctatatgctttgagaaatatggattacgccaaaata
gtgtcatagcagtatgcagcgaaaatagcgcgatcttttctaccccgt
aatcgccgctttatatatgggtatcataacagcaacagtaaatgataac
tacaccgaaagtaagtggaaaacttacaaacatttttttaatcctccatc
atatcgataatcttccaggggaattattcgacactttaaatatttcg
aaacctgaactggtattctgttcgaagaaggcgattaaaaacttgacgc
aattgaagaatcacatcgatttattaaaaagctcgtagttttggatag
tgatgaagacataggtgaagtcgaatctcttgccaactttatgaaacgc
tattcagaatctgttattgatgtgagaaactttaagcctcgcgattttg
atgctaaagaacaagttgccttaatcatgtcgtcatcaggaacaactgg
attacctaaaggagtcgttctaacccatagaaatttgagcgttcgcttt
gtacattgcaagtaggtaacaggaaaaaatttttttgaaactataccta -continued

```
agattgattgtacgttattaatcaaaaatccatgcgcctatattacatg
gtaaagtaggatgtgacacaactgtgtgaaacgtcatcatctactagct
ttttattgatgacgtacatgttgaaataaaatttgaatggcttatacct
taccttagcccaccacattttacctccatttctttgcccctagctgaca
gatccacttccacatcgtttaatcctcttttcagccgatcctgaattcg
aattcaaattcgaattctcttcttctagaagagaattttttctctctttc
cctcttttttctatcttctctagaaaagaattctagaattctaatcctc
ttttcagccgataggatgccctatcggctgccctatctgagtccatcat
ttcaacgatccctagtcatcttagagtgatgaagaatttctacgattta
ttgttctagtattgttcatttactacaaacaaacaatacaataataaag
aatttgaactgtgaattagaaataattcgttcaattttgcacttagtct
taccagtcagtggagttaggttcttagccgtgtattttttaacctcctt
aacaggtctgggttttatatacattttctaacccaatccagacgtata
ttcgtgctcgttattcattattatcctgaccaagccaaatattatccac
agttatggacaggacaggagtcctctcctcataaacttagtgtagttta
attttttcttagggccggtctcgccacctttaataaatttatctgacaa
ataacgtacacaaccggcttctattgtaaaaaatatttaccaaataagt
ttgtcgctggaataactggttttttccggaagatttcaataattagatta
atcttttagggacccgttattcggcacaaggactgtcccttcaacttca
attttatctatcgttcctttccatcatgcgtttggaatgtttacgacgt
tgtcctatttatagtaggactcagagtcatactactaaaaagattcga
agaagaattttttcttaagcactattgaaaagtacagaattccaactatc
gttcttgcaccaccccgtaatggtattcctagccaagagtccgttagtcg
atcagtacgatgtgtccagtattagagaagttgctaccggtggtgcacc
tgtcggcattgaagtggcagaagctgttgcgaaacggtatttgtttttt
tttaattgttgaagtgttgttttataacagttaatgtacaggctaaaa
attaatggaatacttcaaggatacggtctaacagagacatgttgcgccg
tattaatcaccccacacgaccatgttaaaacaggttctactgggaaagt
cgcccgtacgtgcaagcgaaagttgtagatcttagcaccggaaaatct
ctagggccaaataaaagaggagaactttgctttaaaagcgagataatta
tgaaaggttatttcaacaatataaaggctacggaagaggctatcgataa
agaaggatggttacattctggagatgtcgggtattatgatgaagatggt
catttctacgtagtagatcgtttaaaagaacttatcaagtacaagggat
atcaagtatgtcgattttatttaagtgaacgtgtatgaatttaagacc
ctttatgtatttaggttgcaccggctgaattggaatggttgcttttgc
aacatccagctatcaaagacgccggtgttactggcgttcctgacgaagc
tgccggagaacttccgggtgcttgcatagtccttgaagaaggacatagt
cttaccgaacaagaagttattgaatatgtagccggtgagttttagtagc
attttttagttttttaatcaattcgcatttttttcgtagaacgtgtttct
ccaactaaacgtatacgtggtggagtagttttcgttgatgatatacccca
```

-continued

```
aaggagcgactggaaaactcgtcagaagtgaattacggagaatgctttc
tcagaagaaatcgaaactataa
```

The amino acid sequence of SEQ ID NO: 1 which was optimized with respect to human codon is indicated in SEQ ID NO: 3. The gene synthesis was commissioned to Life Technologies, Japan, Co., Ltd. The sequence represented by NO: 3 is indicated below.

SEQ ID NO: 3

```
atgcccaacgagattgtgctgcacggcgccaagcccagggaccctctgg
atctgggcacagccggcagccagctgttcagaagcctgacccagttcag
ctacctgcgcgaggccctggtggacgcccacaccgaacaggtggtgtcc
tacgccgacatcctggaaaacagctgcagactggccatctgcttcgaga
agtacggcctgcggcagaacagcgtgatcgccgtgtgcagcgagaacag
cgccatcttcttctaccctgtgatcgccgccctgtacatgggcatcatc
accgccaccgtgaacgacaactacaccgagagagagctgttcgacaccc
tgaacatcagcaagcccgagctggtgttctgcagcaagaaggccatcaa
gaatctgacccagctgaagaaccacatcgacttcatcaagaaactggtg
gtgctggacagcgacgaggacatcggcgaggtggaaagcctggccaact
tcatgaagcggtacagcgagtccgtgatcgacgtgcggaacttcaagcc
ccgggacttcgacgccaaagaacaggtggccctgatcatgagcagcagc
ggcaccaccggcctgcctaagggcgtggtgctgacccaccggaacctga
gcgtgcgcttcgtgcactgcaaggaccctctgttcggcaccagaaccgt
gcccagcaccagcatcctgagcatcgtgcccttccaccacgccttcggc
atgttcaccaccctgagctacttcatcgtgggcctgagagtgatcctgc
tgaagagattcgaggaagagttcttcctgagcaccatcgagaagtatcg
catccccaccatcgtgctggcccctcccgtgatggtgttcctggccaag
agccccctggtggatcagtacgacgtgtccagcatcagagaggtggcca
ccggcggagcccctgtgggaattgaagtggccgaggccgtggccaagcg
gctgaagatcaacggcatcctgcagggctacggcctgaccgagacatgc
tgcgccgtgctgatccccccacgaccacgtgaaaaccggcagcaccg
gcaaggtggcccctatgtgcaggccaaggtggtggacctgtccaccgg
caagagcctgggccccaacaagcggggcgagctgtgcttcaagagcgag
atcatcatgaagggctacttcaacaacatcaaggccaccgaggaagcca
tcgacaaagagggctggctgcacagcggcgacgtgggctactacgacga
ggacggccacttctacgtggtggaccggctgaaagagctgatcaagtac
aagggctaccaggtggcacctgccgagctggaatggctgctgctgcagc
accccgccatcaaggatgccggcgtgaccggcgtgccagatgaagctgc
tggcgagctgcctggcgcctgtatcgtgctggaagagggccactccctg
accgagcaggaagtgatcgagtacgtcgccgagcgggtgtcccccacca
gagaatcagaggcggcgtggtgttcgtggacgacatccctaagggcgc
cacaggcaagctggtgcgcagcgagctgcggcggatgctgagccagaaa
aagtccaagctgtga
```

The novel luciferase is referred to as a star-worm luciferase in the following.

Example 2

Determination of Enzymatic Parameters of a Novel Luciferase

1. Protein Expression of a Novel Star-Worm Luciferase Gene

For expression in *E. coli*, a star-worm luciferase gene was introduced into a pRSET-B vector (Invitrogen). According to the standard method, the gene expression vector was constructed by the experiments described below.

1-1. Introduction of a Novel Star-Worm Luciferase into an Expression Vector

In order to introduce a luciferase gene encoding the amino acid represented by SEQ ID NO: 1 into a region between BamHI site and EcoRI site of pRSET-B vector, a primer containing initiation codon and recognition sequence of restriction enzyme BamHI GGATCC therebefore, and a primer containing termination codon and recognition sequence of restriction enzyme EcoRI GAATTC thereafter were prepared. With use of this primer pair, a fragment containing the recognition sites of the aforementioned restriction enzyme on both terminals of the luciferase gene was amplified. The PCR was carried out with use of polymerase KOD-Plus (Toyobo Co., Ltd.) according to the manual thereof.

To 20 µl of PCR reaction solution containing 10×PCR Buffer diluted ten fold, dNTP Mixture at a final concentration of 0.2 mM (2.5 mM for each base), $MgSO_4$ at a final concentration of 1.0 mM, Toyobo KOD-Plus (1 U/µl) at a final concentration of 0.02 U/µl, and a primer pair at a final concentration of 0.3 µM, added was 0.4 µl of solution of the luciferase gene not containing BamHI and EcoRI recognition sequences as a template. In the PCR reaction, the reaction solution was thermally denatured for 2 minutes at 94° C., and then the cycle consisting of 30 seconds at 94° C., 30 seconds at 55° C., and 2 minutes at 68° C. was repeated 30 times, followed by elongation reaction at 68° C. for 5 minutes. After the PCR reaction, 1 µl of PCR reaction solution was applied to 1% TAE agarose gel electrophoresis, and observed bands of amplified genes under exposure of ultraviolet after dyeing with ethidium bromide. The gene amplification was confirmed, and thus this PCR reaction solution was precipitated and concentrated by an ethanol precipitation method, dissolved by adding 4 µl of 10×H Buffer for restriction enzyme treatment, restriction enzymes BamHI (Toyobo Co., Ltd.) and EcoRI (Toyobo Co., Ltd.) of 2 µl each, and 32 µl of sterile deionized ion water, and treated with the restriction enzymes, maintaining the temperature at 37° C. for 2 hours. Subsequently, the reaction solution was precipitated and concentrated by the ethanol precipitation method, and dissolved in sterile deionized ion water. The solution was applied to 1% TAE agarose gel electrophoresis, followed by dyeing with ethidium bromide. The gel containing DNA bands which were confirmed under exposure of ultraviolet were clipped out by a knife. From the clipped gel, DNA was extracted with use of Wizard® SV Gel and PCR Clean-UP System (Promega KK). These operations were performed according to the manual. Subsequently, with use of Ligation Pack (Nippon Gene) in accordance with the manual, the extracted DNA was introduced into a pRSET-B vector which was treated by BamHI and EcoRI in advance by the same method. This vector DNA was transformed to *E. coli* JM109 (DE3) strain and allowed colony formation.

A direct colony PCR was carried out using the obtained colony as a template, and the luciferase gene introduced into pRSET-B was amplified. The direct colony PCR was performed with use of a primer pair of T7 promoter Primer (5'-TAA TAC GAC TCA CTA TAG GG-3': SEQ ID NO: 10) and T7 Reverse Primer (5'-CTA GTT ATT GCT CAG CGG TGG-3': SEQ ID NO: 11). To 10 µl of PCR reaction solution containing 10×Ex Taq Buffer (20 mM $Mg^{2+}$ plus) diluted tenfold, dNTP Mixture at a final concentration of 0.2 mM (2.5 mM for each base), TaKaRa Ex Taq (5 U/µl) at a final concentration of 0.05 U/µl, and primers at a final concentration of 0.2 µM, added was a small amount of *E. coli* colony as a template. In the PCR reaction, the solution was thermally denatured for 2 minutes at 94° C., and then the cycle consisting of 30 seconds at 94° C., 30 seconds at 50° C., and 2 minutes at 72° C. was repeated 25 times, followed by an elongation reaction at 72° C. for 5 minutes. After the PCR reaction, 1 µl of the PCR reaction solution was applied to 1% TAE agarose gel electrophoresis, and observed bands of amplified genes under exposure of ultraviolet after dyeing with ethidium bromide.

Regarding the PCR reaction solution for which amplification was confirmed, the base sequence of the gene was determined by a direct sequencing method. With use of PCR product purification kit ExoSAP-IT, the extra dNTP and primers were removed thereby preparing a template for PCR direct sequencing. The sequencing reaction solution containing the template was prepared by using BigDye Terminator v3.1 Cycle Sequencing Kit, and a sequencing reaction was carried out with use of a thermal cycler. A vector primer or a gene-specific primer was used for sequencing. Purification and sequencing of the PCR product were carried out according to the manual. After a sequencing reaction, the reaction product was purified as explained below. 100% ethanol of 2.5 times of weight was added to the reaction solution, and the nucleic acid was precipitated by a centrifuge. After removing the supernatant, the precipitate was washed by adding 70% ethanol, and the nucleic acid was precipitated by a centrifuge. After removing the supernatant, the precipitate was finally dried. The purified precipitate was dissolved by adding 15 µl of Hi-Di Formamide (Applied Biosystems). The solution was thermally denatured for 2 minutes at 94° C., cooled on ice, and used as a sample for determination of the base sequence. With respect to the sample, the base sequence was determined by Applied Biosystems 3130x1 Genetic Analyzer, and confirmed that the gene was introduced into a gene expression vector pRSET-B.

2. Purification of a Luminescent Protein 0.5 µl of a luciferase expression vector was added to 50 µl of the *E. coli* solution containing JM109 (DE3), and the solution was incubated on ice for 10 minutes, then at 42° C. for 1 minute, and incubated on ice for 2 minutes. Subsequently, 50 µl of the *E. coli* solution was added to 200 µl of SOC culture medium, and incubated during shaking for 20 minutes at 37° C. LB culture medium plate (containing 100 µg/ml of Ampicillin) was streaked with 100 µl of the incubated sample and incubated at 37° C. overnight. On the next day, the obtained colony was incubated in LB culture medium of 500 ml scale at 37° C. for 24 hours and at 18° C. for 24 hours. After the incubation of total 48 hours, the fungus body was collected by a centrifuge, resuspended in 0.1 M Tris-HCl solution (pH 8.0), and subjected to be ultrasonic fragmentation. The fragmented solution of the fungus body was subjected to centrifuge separation (15,000 rpm, 10 minutes), and the precipitate was removed and the supernatant was collected. To the column having 2 ml of a bed volume, 500 µl of Ni-Agar suspension solution and 2 ml of 0.1 M Tris-HCl were added to equilibrate the column. The collected supernatant was added to the column, and let it pass through the column. While all the supernatant was passed through the column, the operations were all carried out at 4° C. The column was washed with 2 ml of 25 mM imidazole/0.1 M Tris-HCl solution. To the washed column, 2 ml of 500 mM imidazole/0.1 M Tris-HCl solution was added to elute a luciferase. The eluted sample was filtrated with gel filtration column PD-10 (GE Healthcare) and demineralized. The demineralized sample was subjected to ultrafiltration with Vivaspin6 (Sartorius K.K.), and glycerin was added to the concentrated sample to prepare 50% glycerine solution. The solution was preserved at −20° C.

3. Measurement of Luminescence Spectra

With use of LumiFlSpectroCapture (ATTO) as an apparatus for measurement, to a solution of 0.1 M citric acid/0.1 M $Na_2HPO_4$ buffer (pH 6.0-8.0) containing 1 mM D-luciferin, 2 mM of ATP and 4 mM $MgCl_2$, the purified enzyme was added at a final concentration of 1 to 10 μg/ml, and luminescence spectra were measured after 15 seconds of addition of the enzyme. The measurement results were shown in FIG. 1.

FIG. 1 shows that the obtained luciferase induces luminescence such that a maximum luminous wavelength falls within a range of 557 to 562 nm over the entire pH range of 5.5 to 8.0. More specifically, it induces luminescence such that a maximum luminous wavelength is around 562 nm in an environment of pH 8.0. Further, it induces luminescence such that a maximum luminous wavelength is around 559 nm, 557 nm, 557 nm, 557 nm, 557 nm, in an environment of pH 7.5, pH 7.0, pH 6.5, pH 6.0, and pH 5.5, respectively.

4. Kinetic Analysis 4-1. Determination of Concentrations of D-Luciferin and ATP

A concentration of D-luciferin in D-luciferin solution and that of ATP in ATP solution were determined as described below.

With use of UV-Visible Spectrometer (Hitachi), ultraviolet visible absorption spectra were measured for the D-luciferin solution and ATP solution. Based on the measurement results and r values indicated below, concentrations of the solutions were calculated.

D-luciferin: $\lambda$max 328 nm, E 18200, pH 5.0
ATP: $\lambda$max 259 nm, $\epsilon$ 15400, pH 7.0

The measurements were carried out ten times for each sample, and the average of absorbance was used for the calculation. The Km values were calculated by using the D-luciferin solution and ATP solution whose concentrations were determined in the aforementioned manner.

4-2. Measurement of Km for D-Luciferin

Under various concentrations of D-luciferin, the luminous intensity was measured for the obtained luciferase. Based on the measurement results, Km values with respect to D-luciferin were calculated.

Eight types of D-luciferin solutions of various concentrations were prepared by adding D-luciferin to 0.1 M Tris-HCl (pH 8.0). These solutions contain D-luciferin at final concentrations of 0.625, 1.25, 2.5, 5, 10, 20, 40, and 80 μM. These D-luciferin solutions were each injected into 96-well microplate at an amount of 50 μl. A solution of 0.1 M Tris-HCl (pH 8.0) containing each purified luciferase, 4 mM of ATP, and 8 mM of $MgSO_4$ was connected to the standard pump of a luminometer, and measurement was carried out at the same time of adding 50 μl of the solution to the well. A Luminescensor (ATTO) was used for the measurement. Measurement was repeated three times for each luciferin concentration.

The peak intensity of the obtained photon count value was plotted with respect to luciferin concentration S, defining the initial rate as V. The plots were subjected to curve fitting of Michaelis Menten type, thereby giving Km values. The curve fitting was performed by a nonlinear least-squares method, and search of parameter was performed by a Newton method.

4-3. Measurement of Km Value with Respect to ATP

Under various ATP concentrations, the luminous intensity of the obtained luciferase was measured. Based on the results, Km values was determined with respect to ATP.

Various eight types of ATP solutions were prepared by adding ATP to 0.1 M Tris-HCl (pH 8.0). These solutions contain ATP at final concentration of 10, 20, 40, 80, 160, 320, 480, or 640 μM. These ATP solutions were each injected into a 96-well microplate at a volume of 50 μl. 0.1 M Tris-HCl (pH 8.0) solution containing each purified luciferase, 1 mM D-luciferin, and 8 mM $MgSO_4$ was connected to the standard pump of the luminometer, and measurement was carried out at the same time of addition of 50 μl of the solution to wells. Measurement was repeated three times for each ATP concentration.

The peak intensity of the obtained photon count value was plotted with respect to ATP concentration S, defining an initial rate as V. The plots were subjected to curve fitting of Michaelis Menten type, thereby giving Km value. The curve fitting was performed by a nonlinear least-squares method, and the search of parameter was performed by a Newton method.

In Table 1, Km values were shown with respect to D-luciferin and to ATP which were determined as described above. Table 1 indicates Km values for a known luciferase as well, which were measured in a similar manner. GL3 is a luciferase derived from *P. pyralis*. Further, ELuc, CBG, and CBR are luciferases derived from known click beetles. These known were commercially available.

TABLE 1

Comparison of Km value

| | Km | |
|---|---|---|
| | D-luciferin (uM) | ATP (uM) |
| Diplocladon sp | 38.9 | 110 |
| GL3 | 15.7 | 64.3 |
| ELuc | 12.7 | 182 |
| CBG | 1.44 | 58.4 |
| CBR | 33.3 | 47 |

FIG. 2 indicates these Km values as plots with respect to D-luciferin concentration and ATP concentration.

Example 3

Measurement of Luminous Intensity

The luminous intensities when expressed in a HeLa cell were compared between a star-worm luciferase and *P. pyralis* luciferase.

Regarding a star-worm luciferase, Kozak sequence was added to a nucleic acid optimized for expression in a mammalian cell and then inserted into between SgfI site and PmeI site of a multicloning site of pF9A CMV hRLuc neo Flexi vector (Promega). According to addition of Kozak sequence, an amino acid encoded by the codon immediately after initiation codon, proline, was changed to alanine. A pF9A vector contains in the vector sequence a luciferase gene derived from sea pansy as an internal control, and luminous intensity by the luminescent gene inserted into the multicloning site can be calculated as a ratio to that by the sea pansy luciferase. For the purpose of comparison, Kozak sequence was added to a known *P. pyralis* nucleic acid containing an optimized gene for expression in a mammalian cell, and then inserted into apF9A CMV hRLuc neo Flexi vector in a similar manner.

Each of the two types of plasmids obtained by the aforementioned manner was introduced into HeLa cells by means of lipofection method, and 24 hours later the cells were washed with PBS. To each well of a 24-well plate, 500 μl of 2 mM D-luciferin/CO2 Independent Medium (Invitrogen) was added, and luminous intensity was measured for 90 minutes with use of Luminescensor (ATTO) under the condition of 25° C. and 1 second per well. The luminous intensity at a time point of after a lapse of 90 minutes was used as luminous intensity of a star-worm luciferase and *P. pyraris* luciferase. After removing the culture medium from each well, the wells were washed with PBS three times. Subsequently, 500 μl of 10 μl coelenterazine/CO2 Independent Medium was added to each well, and luminous intensity was measured for 30 minutes with use of Luminescensor under the measurement condition of 25° C. and 1 second per well. After addition of coelenterazine, luminous intensity of at a time point of after a lapse of minutes was used as the luminous intensity of the internal control sea pansy luciferase. The luminous intensities of a star-worm luciferase and *P. Pyralis* were each divided by the luminous intensity of a sea pansy luciferase, and the obtained value was indicated in a graph as the luminous intensity of each luciferase. The results are shown in FIG. 3. According to the figure, the star-worm luciferase induced luminescence having 1.5 times the luminous intensity in a HeLa cell of that induced by *P. Pyralis* luciferase.

Example 4

Stabilization of a Star-Worm Luciferase

The luminous intensities were compared between a star-worm mutant luciferase and a star-worm wild-type luciferase having the amino acid sequence represented by SEQ ID NO: 1.

First, a star-worm mutant luciferase was prepared. Into a vector prepared in Example 3 containing a star-worm wild-type luciferase gene in which a codon was optimized and to which Kozak sequence was added, mutation was introduced with use of a primer for mutation introduction (represented by SEQ ID NO: 12). The star-worm mutant luciferase obtained thereby encodes a luciferase in which cysteine at position 344 is substituted by serine. The mutation was introduced according to a method described in Asako Sawano and Atsushi Miyawaki, Nuleic Acids Research, 2000, Vol. 28, No. 16, E78. After introduction of mutation, it was confirmed that the aimed mutation was introduced, by determining the sequence by means of sequencing. The base sequence of the obtained mutant and the amino acid sequence thereof are indicated in SEQ ID NOS: 13 and 14. In the amino acid sequence represented by SEQ ID NO: 14, the amino acid at position 2 is alanine, which was changed from proline in accordance with addition of Kozak sequence. The amino acid sequence without Kozak sequence containing only C344S mutation is represented by SEQ ID NO: 15. The sequences represented by NOS: 13 and 15 are indicated below.

```
                                           SEQ ID NO: 13
atggccaacgagattgtgctgcacggcgccaagcccagggaccctctgg atctgggcacagccggcagccagctgttcagaagcctgacccagttcag ctacctgcgcgaggccctggtggacgcccacaccgaacaggtggtgtcc tacgccgacatcctggaaaacagctgcagactggccatctgcttcgaga agtacggcctgcggcagaacagcgtgatcgccgtgtgcagcgagaacag cgccatcttcttctaccctgtgatcgccgccctgtacatgggcatcatc accgccaccgtgaacgacaactacaccgagagagagctgttcgacaccc tgaacatcagcaagcccgagctggtgttctgcagcaagaaggccatcaa gaatctgacccagctgaagaaccacatcgacttcatcaagaaactggtg gtgctggacagcgacgaggacatcggcgaggtggaaagcctggccaact tcatgaagcggtacagcgagtccgtgatcgacgtgcggaacttcaagcc ccgggacttcgacgccaaagaacaggtggccctgatcatgagcagcagc ggcaccaccggcctgcctaagggcgtggtgctgacccaccggaacctga gcgtgcgcttcgtgcactgcaaggaccctctgttcggcaccagaaccgt gcccagcaccagcatcctgagcatcgtgcccttccaccacgccttcggc atgttcaccacccctgagctacttcatcgtgggcctgagagtgatcctgc tgaagagattcgaggaagagttcttcctgagcaccatcgagaagtatcg catccccaccatcgtgctggcccctcccgtgatggtgttcctggccaag agcccctggtggatcagtacgacgtgtccagcatcagagaggtggcca ccggcggagcccctgtgggaattgaagtggccgaggccgtggccaagcg gctgaagatcaacggcatcctgcagggctacggcctgaccgagacatgc agcgccgtgctgatcaccccccacgaccacgtgaaaaccggcagcaccg gcaaggtggccccctatgtgcaggccaaggtggtggacctgtccaccgg caagagcctgggccccaacaagcggggcgagctgtgcttcaagagcgag atcatcatgaagggctacttcaacaacatcaaggccaccgaggaagcca tcgacaaagagggctggctgcacagcggcgacgtgggctactacgacga ggacggccacttctacgtggtggaccggctgaaagagctgatcaagtac aagggctaccaggtggcacctgccgagctggaatggctgctgctgcagc accccgccatcaaggatgccggcgtgaccggcgtgccagatgaagctgc tggcgagctgcctggcgcctgtatcgtgctggaagagggccactccctg accgagcaggaagtgatcgagtacgtcgccgagcgggtgtcccccacca agagaatcagaggcggcgtggtgttcgtggacgacatccctaagggcgc cacaggcaagctggtgcgcagcgagctgcggcggatgctgagccagaaa aagtccaagctgtga
```

```
                                           SEQ ID NO: 15
MPNEIVLHGAKPRDPLDLGTAGSQLFRSLTQFSYLREALVDAHTEQVVS

YADILENSCRLAICFEKYGLRQNSVIAVCSENSAIFFYPVIAALYMGII

TATVNDNYTERELFDTLNISKPELVFCSKKAIKNLTQLKNHIDFIKKLV

VLDSDEDIGEVESLANFMKRYSESVIDVRNFKPRDFDAKEQVALIMSSS

GTTGLPKGVVLTHRNLSVRFVHCKDPLFGTRTVPSTSILSIVPFHHAFG

MFTTLSYFIVGLRVILLKRFEEEFFLSTIEKYRIPTIVLAPPVMVFLAK
```

-continued

SPLVDQYDVSSIREVATGGAPVGIEVAEAVAKRLKINGILQGYGLTETC

SAVLITPHDHVKTGSTGKVAPYVQAKVVDLSTGKSLGPNKRGELCFKSE

IIMKGYFNNIKATEEAIDKEGWLHSGDVGYYDEDGHFYVVDRLKELIKY

KGYQVAPAELEWLLLQHPAIKDAGVTGVPDEAAGELPGACIVLEEGHSL

TEQEVIEYVAERVSPTKRIRGGVVFVDDIPKGATGKLVRSELRRMLSQK

KSKL

The pF9A vector used herein contains a sea pansy luciferase gene in the vector sequence as an internal control, and the luminous intensity of the luminescent gene inserted into the multicloning site can be calculated as a ratio to that of a sea pansy luciferase.

The plasmid of star-worm mutant luciferase obtained as mentioned above and the plasmid of star-worm wild-type luciferase obtained in Example 3, in which a codon was optimized and to which Kozak sequence was added, were each introduced into HeLa cells by means of the lipofection method, and the cells were washed with PBS 24 hours later. To each well of a 48-well plate, 500 µl of 2 mM D-luciferine/CO2 Independent Medium (Invitrogen) was added, and luminous intensity was measured for 90 minutes under the measurement condition of 37° C. for 1 second per well with use of Luminescensor. The luminous intensity at a time point of after a lapse of 90 minutes was used as luminous intensity of each luciferase. After removing the culture medium from each well, each well was washed with PBS three times. Subsequently, 500 µl of 10 µM coelenterazine/CO2 Independent Medium was added to each well, and the luminous intensity was measured for 30 minutes under the measurement condition of 37° C. for 1 second per well. After addition of coelenterazine, the luminous intensity obtained at the time point of after a lapse of 5 minutes was used as luminous intensity of the internal control sea pansy luciferase. The luminous intensities of a star-worm wild-type luciferase and mutant luciferase were each divided by the luminous intensity of the sea pansy luciferase, and the obtained values were indicated in a graph as the luminous intensity of each luciferase. The results are shown in FIG. 4. According to the figure, the star-worm mutant luciferase induces luminescence having 4.9 times the luminous intensity of that induced by the star-worm wild-type luciferase in a HeLa cell.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A luciferase having an amino acid sequence comprising SEQ ID NO: 15.

2. The luciferase according to claim 1, inducing luminescence such that a maximum luminous wavelength falls within a range of 557 to 562 nm over the entire pH range of 5.5 to 8.0.

3. The luciferase according to claim 1, inducing luminescence having 1.5 times the luminous intensity of luminescence induced by *Photinus pyralis* firefly luciferase.

* * * * *